(12) United States Patent  
Maxton et al.

(10) Patent No.: US 6,497,032 B2
(45) Date of Patent: Dec. 24, 2002

(54) REFASTENABLE BONDING OF GARMENT SIDE PANELS

(75) Inventors: David Albert Maxton, Menasha, WI (US); Megan Elizabeth Clemmensen, Roswell, GA (US); Chris Alan Pettit, Oshkosh, WI (US); Steven John Shimon, Sherwood, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 67 days.

(21) Appl. No.: 09/855,450

(22) Filed: May 15, 2001

(65) Prior Publication Data

US 2002/0003021 A1 Jan. 10, 2002

Related U.S. Application Data

(60) Provisional application No. 60/204,494, filed on May 16, 2000.

(51) Int. Cl.[7] .................................................. A61F 13/15
(52) U.S. Cl. .......................... 29/429; 156/226; 156/227
(58) Field of Search .................................. 156/226, 227, 156/582; 493/416, 419, 422, 424, 435, 434, 436, 442, 454; 29/428, 429

(56) References Cited

U.S. PATENT DOCUMENTS

| 1,912,466 A | 6/1933 | Remington |
|---|---|---|
| 1,912,724 A | 6/1933 | Remington |
| 2,037,561 A | 4/1936 | Blosser et al. |

(List continued on next page.)

FOREIGN PATENT DOCUMENTS

| EP | 0 217 032 A2 | 4/1987 |
|---|---|---|
| EP | 0 320 989 A2 | 6/1989 |
| EP | 0 532 486 A1 | 3/1993 |
| EP | 0 631 766 A1 | 1/1995 |
| EP | 0 689 816 A2 | 1/1996 |
| EP | 0 753 292 A2 | 1/1997 |
| EP | 0 761 193 A2 | 3/1997 |
| EP | 0 800 808 A1 | 10/1997 |
| EP | 0 803 602 A1 | 10/1997 |
| EP | 0 820 747 A1 | 1/1998 |
| EP | 0 934 739 A2 | 8/1999 |
| FR | 2 299 254 | 8/1976 |
| GB | 1 384 622 | 2/1975 |
| GB | 1 593 600 | 7/1981 |
| GB | 2 160 817 A | 1/1986 |
| GB | 2 288 314 A | 10/1995 |
| WO | WO 91/19613 A1 | 12/1991 |
| WO | WO 95/18589 A1 | 7/1995 |
| WO | WO 95/18591 A2 | 7/1995 |
| WO | WO 95/27462 A1 | 10/1995 |
| WO | WO 95/32639 A1 | 12/1995 |
| WO | WO 95/33618 A1 | 12/1995 |
| WO | WO 97/23180 A1 | 7/1997 |
| WO | WO 97/24098 A1 | 7/1997 |
| WO | WO 98/15248 A1 | 4/1998 |
| WO | WO 99/65441 A1 | 12/1999 |
| WO | WO 00/35395 A2 | 6/2000 |
| WO | WO 00/37009 A2 | 6/2000 |

Primary Examiner—Michael W. Ball
Assistant Examiner—Barbara J Musser
(74) Attorney, Agent, or Firm—Thomas M. Gage

(57) ABSTRACT

In a process for making prefastened and refastenable garments, a discrete article is transported in a primary direction of movement. The discrete article can define a leading half comprising first fastening components, a trailing half comprising second fastening components releasably engageable with the first fastening components, and an interconnecting region disposed between and interconnecting the leading and trailing halves. The leading half can be temporarily diverted from the primary direction of movement, while continuing to transport the interconnecting region and the trailing half in the primary direction. After reestablishing movement of the leading half in the primary direction, the leading half can contact a contoured surface, such as a contoured plate or roll. The contact can cause the first fastening components to be transversely displaced toward one another, whereupon the first and second fastening components can be engaged.

30 Claims, 14 Drawing Sheets

U.S. PATENT DOCUMENTS

| | | |
|---|---|---|
| 2,714,230 A | 8/1955 | Young |
| 3,116,920 A | 1/1964 | Geer et al. |
| 3,502,322 A | 3/1970 | Cran |
| 3,632,030 A | 1/1972 | Cohn et al. |
| 3,808,767 A | 5/1974 | Reid |
| 3,870,292 A | 3/1975 | Bradley |
| 3,874,043 A | 4/1975 | Holm |
| 3,918,706 A | 11/1975 | Craft |
| 3,994,486 A | 11/1976 | Nystrand |
| 4,018,432 A | 4/1977 | Frick |
| 4,053,967 A | 10/1977 | Mair |
| 4,170,347 A | 10/1979 | Lewis |
| 4,186,860 A | 2/1980 | Reba |
| 4,197,621 A | 4/1980 | Mair |
| 4,279,610 A | 7/1981 | Reba |
| 4,323,534 A | 4/1982 | DesMarais |
| 4,342,413 A | 8/1982 | Reba |
| 4,418,513 A | 12/1983 | Plahm |
| 4,453,709 A | 6/1984 | Reba |
| 4,479,640 A | 10/1984 | Smith |
| 4,516,760 A | 5/1985 | Stumpf |
| 4,543,154 A | 9/1985 | Reiter |
| 4,597,573 A | 7/1986 | Reba et al. |
| 4,640,726 A | 2/1987 | Sallee et al. |
| 4,663,106 A | 5/1987 | Pomplun et al. |
| 4,663,220 A | 5/1987 | Wisneski et al. |
| 4,665,306 A | 5/1987 | Roland et al. |
| 4,702,468 A | 10/1987 | Pollich |
| 4,704,116 A | 11/1987 | Enloe |
| 4,710,189 A | 12/1987 | Lash |
| 4,717,375 A | 1/1988 | Lundmark |
| 4,750,442 A | 6/1988 | Keeton |
| 4,808,252 A | 2/1989 | Lash |
| 4,834,738 A | 5/1989 | Kielpikowski et al. |
| 4,865,579 A | 9/1989 | Kirby et al. |
| 4,875,668 A | 10/1989 | Spyra |
| 4,883,549 A | 11/1989 | Frost et al. |
| 4,885,853 A | 12/1989 | McCabe |
| 4,936,840 A | 6/1990 | Proxmire |
| 4,940,464 A | 7/1990 | Van Gompel et al. |
| 5,046,272 A | 9/1991 | Vogt et al. |
| 5,092,863 A | 3/1992 | Schanzlin |
| 5,093,422 A | 3/1992 | Himes |
| 5,104,116 A | 4/1992 | Pohjola |
| 5,110,403 A | 5/1992 | Ehlert |
| 5,140,757 A | 8/1992 | Terada |
| 5,176,615 A | 1/1993 | Munsch |
| 5,184,555 A | 2/1993 | Quadracci et al. |
| 5,197,722 A | 3/1993 | Adamski, Jr. et al. |
| 5,199,623 A | 4/1993 | Rajala et al. |
| 5,224,405 A | 7/1993 | Pohjola |
| 5,226,992 A | 7/1993 | Morman |
| 5,300,007 A | 4/1994 | Kober |
| 5,304,599 A | 4/1994 | Himes |
| 5,330,598 A | 7/1994 | Erdman et al. |
| 5,344,691 A | 9/1994 | Hanschen et al. |
| 5,353,979 A | 10/1994 | Gartmann |
| 5,363,784 A | 11/1994 | Adamski, Jr. et al. |
| 5,399,219 A | 3/1995 | Roessler et al. |
| 5,435,802 A | 7/1995 | Kober |
| 5,556,360 A | 9/1996 | Kober et al. |
| 5,660,666 A | 8/1997 | Dilnik et al. |
| 5,705,013 A | 1/1998 | Nease et al. |
| 5,765,495 A | 6/1998 | Adamski, Jr. |
| 5,766,389 A | 6/1998 | Brandon et al. |
| 5,779,831 A | 7/1998 | Schmitz |
| 5,788,805 A | 8/1998 | Herrmann |
| 5,795,433 A | 8/1998 | Niedermeyer |
| 5,803,448 A | 9/1998 | Stiel et al. |
| 5,807,368 A | 9/1998 | Helmer |
| 5,858,515 A | 1/1999 | Stokes et al. |
| 5,865,135 A | 2/1999 | Price et al. |
| 5,904,802 A | 5/1999 | Niedermeyer |
| 5,915,319 A | 6/1999 | Price et al. |
| 5,916,203 A | 6/1999 | Brandon et al. |
| 5,919,334 A | 7/1999 | Niedermeyer |
| 5,997,981 A | 12/1999 | McCormack et al. |
| 6,022,431 A | 2/2000 | Blenke et al. |
| 6,022,432 A | 2/2000 | Elsberg et al. |
| 6,027,440 A | 2/2000 | Roth |
| 6,036,805 A | 3/2000 | McNichols |
| 6,113,717 A | 9/2000 | Vogt et al. |

REFASTENABLE BONDING OF GARMENT SIDE PANELS

This application claims priority from U.S. Provisional Application No. 60/204,494 filed on May 16, 2000.

BACKGROUND OF THE INVENTION

The present invention pertains to processes and apparatus for making garments, and more particularly to processes and apparatus for folding and bonding disposable absorbent garments.

Garments such as disposable absorbent garments have numerous applications including diapers, training pants, feminine care products, and adult incontinence products. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

One form of disposable absorbent garment is a two-dimensional product that has open sides. Two-dimensional products, such as conventional diapers and some adult incontinence products, are generally flat and provided in an unfastened configuration. These garments have typically included fasteners such as adhesive tape fasteners or hook and loop type fasteners that releasably connect the front and back waist portions to secure the product about the wearer. Two-dimensional product can be easily applied or removed while the wearer is lying down.

Another form of disposable absorbent garment is a three-dimensional product with closed sides so that the product has a unitary waist opening and two leg openings. The wearer raises and lowers the garment to apply the product. Three-dimensional products are particularly appealing because the pant has a very garment-like look. Children for instance identify diaper products with babies, and most children do not like being identified with or as babies. Consequently, these children do not want to wear baby diapers, and instead prefer to wear training pants that look like adult underwear. Thus, the switch from a traditional diaper to a more garment-like or underwear-like training pant can be an important step in the toilet training process. Similarly, adults seeking the protection of incontinence products prefer the normalcy of a pant product rather than an incontinence product that must be applied in another fashion. Three-dimensional garments have been designed such that they can be torn to remove the garment from the wearer after it has been soiled.

Recently, prefastened and refastenable disposable absorbent garments have been proposed to provide the advantages of both two-dimensional and three-dimensional products. Prefastened and refastenable products can be applied and/or removed either like a conventional diaper or like a conventional training pant. For use as training pants, for example, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied like either a diaper or a pant permits the interior of the product to be easily checked without having to pull the product downward.

Disposable absorbent products present many manufacturing challenges. In part, this is due to the high speed that is necessary to economically produce relatively low cost disposable absorbent products. Further, prefastened and refastenable garments present new challenges for high speed manufacturing. Such products must incorporate refastenable fasteners that are properly aligned and engaged. Improperly attached or aligned fasteners can lead to many product deficiencies, including machine waste and/or delay, improper fit, fastener delamination during use, fastener disengagement during use, skin irritation, or the like.

Thus, what is lacking and needed in the art are improved processes and apparatus for folding and bonding disposable absorbent garments, including prefastened disposable absorbent garments.

SUMMARY OF THE INVENTION

In response to the above-referenced unfulfilled need in the art, new processes and apparatus for folding and bonding disposable absorbent garments, including prefastened disposable absorbent garments, have been discovered. One aspect of the invention concerns a process for making a prefastened and refastenable garment. The process comprises transporting a discrete article in a primary direction of movement. The discrete article defines a leading half comprising first fastening components, a trailing half comprising second fastening components releasably engageable with the first fastening components, and an interconnecting region disposed between and interconnecting the leading and trailing halves. The leading half is temporarily diverted from the primary direction of movement while continuing to transport the interconnecting region and the trailing half in the primary direction of movement. Movement of the leading half in the primary direction of movement is reestablished. The method also comprises contacting the leading half with a contoured surface, such that the first fastening components are transversely displaced toward one another. The transversely displaced first fastening components can be moved into contact with the second fastening components.

In another embodiment, the process for making a prefastened and refastenable garment comprises: transporting a discrete article on a primary transport surface in a primary direction of movement; drawing the leading half onto a secondary transport surface traveling in a secondary direction of movement divergent from the primary direction of movement while continuing to transport the interconnecting region and the trailing half in the primary direction of movement; releasing the leading half from the secondary transport surface; contacting the leading half with a contoured surface, wherein the first fastening components are transversely displaced toward one another; and pressing the leading and trailing halves together with the transversely displaced first fastening components releasably engaging the second fastening components.

In another embodiment, a process for making prefastened and refastenable garments comprises: providing main and secondary folding drums in close proximity to one another and defining a tangent point therebetween; rotating the main and secondary folding drums in opposite directions; introducing a plurality of discrete articles onto the main folding drum, each discrete article defining a leading half comprising first fastening components, a trailing half comprising second fastening components releasably engageable with the first fastening components, and an interconnecting region disposed between and interconnecting the leading and trailing halves; drawing the leading half of a discrete article onto the secondary folding drum as the leading half passes the tangent point, and continuing to transport the interconnecting region and the trailing half on the main folding drum; releasing the leading half from the secondary folding drum such that the interconnecting region remains on the main folding drum; contacting the leading half with a contoured surface, wherein the first fastening components are transversely displaced toward one another; and pressing the leading and trailing halves together with the transversely displaced first fastening components releasably engaging the second fastening components.

Through contact with the contoured surface, the distance between the first fastening components can be reduced from an initial distance to a post displacement distance. The post displacement distance can correspond to the distance between the second fastening components. In particular embodiments, side panels of the trailing half can be folded to invert the second fastening components and reduce the distance between the second fastening components to a post inversion distance. The post inversion distance can be substantially equal to the post displacement distance. In the context of the present invention, the distance between the first fastening components and the distance between the second fastening components both refer to the transverse linear distance between the fastening components. "Transverse linear distance" is used herein to refer to the distance between two fastening components, measured in a straight line parallel to the transverse axis of the garment without regard to surface contours of the garment. There may or may not be any force exerted in the transverse direction at the time of measurement.

Another aspect of the invention concerns an apparatus for making prefastened and refastenable garments. In one embodiment, the apparatus comprises a main folding drum rotatively mounted to define a primary direction of movement and a secondary folding drum rotatively mounted in close proximity to the main folding drum. A contoured surface is disposed in close proximity to the main folding drum downstream from the secondary folding drum. The contoured surface has a central section and flanges outward from the central section, and the flanges are positioned closer to the main folding drum than the central section.

The contoured surface can comprise a contoured guide plate. The contoured guide plate can have an upstream edge, an opposite downstream edge, a central section extending between the upstream and downstream edges, and a pair of flanges outward from the central section. To generate transverse displacement of fastening components, the central section and the flanges can have greater vertical separation toward the downstream edge.

In another embodiment, the apparatus comprises a main folding drum rotatively mounted to define a primary direction of movement, a secondary folding drum rotatively mounted in close proximity to the main folding drum, and a contoured roll rotatively mounted in close proximity to the main folding drum downstream from the secondary folding drum. The contoured roll and the secondary folding drum both rotate in a direction opposite that of the main folding drum. The contoured roll comprises a central section and flanges axially outward from the central section, and the contoured roll has a larger diameter at the flanges than at the central section.

The flanges of the contoured roll can form a nip with the main folding drum. Furthermore, the contoured roll can comprise a vacuum roll.

The fastening components to form refastenable seams can comprise separate elements bonded to another component of the pant. Alternatively, the fastening components can comprise a portion of another element of the pant, such as the bodyside liner, the outer cover, separate side panels if employed, integral side panels if employed, a belt-type component extending transversely across the chassis if employed, or the like. Thus, unless otherwise specified, the term "fastening component" includes separate components which function as fasteners and regions of materials such as side panels, liners, outer covers or the like which function as fasteners. Moreover, a single material can define multiple fastening components to the extent that different regions of the material function as separate fasteners. The fastening components can be located on the side panels, between the side panels such as on the absorbent chassis, or a combination of the two. The fastening components can have any desired shape, such as square, rectangular, round, curved, oval, irregularly shaped, or the like. Each fastening component can comprise a single fastening element or multiple fastening elements.

The fastening components can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

A refastenable fastening system allows for easy inspection of the interior of the pant-like product. If necessary, the fastening system also allows the pant to be removed quickly and easily. This is particularly beneficial when the pant contains messy excrement. For training pants, the caregiver can completely remove the pant-like product and replace it with a new one without having to remove the child's shoes and clothing.

The present invention can be used in the manufacture of a wide variety of absorbent and non-absorbent products, including training pants, swim pants, diaper pants, incontinence garments, feminine care products, health care garments, apparel for institutional, industrial and consumer use, or other garments using mechanical or adhesive fasteners. Absorbent articles are adapted to be worn adjacent to the body of a wearer to absorb and contain various exudates discharged from the body. The absorbent articles can be prefastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

Particular training pants suitable for use with the present invention are disclosed in U.S. patent application Ser. No. 09/444,083, filed on Nov. 22, 1999 (corresponding to PCT application WO 00/37009 published Jun. 29, 2000) by A. Fletcher et al. and titled "Absorbent Articles With Refastenable Side Seams;" which is incorporated herein by reference. This reference describes various materials and methods for constructing training pants. Training pants can also be constructed using the methods and apparatus disclosed in U.S. Pat. 4,940,464 issued Jul. 10,1990 to Van Gompel et al.; and U.S. Pat. 5,766,389 issued Jun. 16, 1998 to Brandon et al.; which are also incorporated herein by reference.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The methods and apparatus of the present invention can be used to make a variety of garments. Examples of such garments include disposable absorbent articles such as diapers, training pants, feminine hygiene products, incontinence products, other personal care or health care garments; swim pants; athletic clothing; pants and shorts; or the like. For ease of explanation, the description hereafter will be in terms of methods and apparatus for making a child's training pant. In particular, the methods and apparatus will be described in terms of those for making prefastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference.

Figure 1:
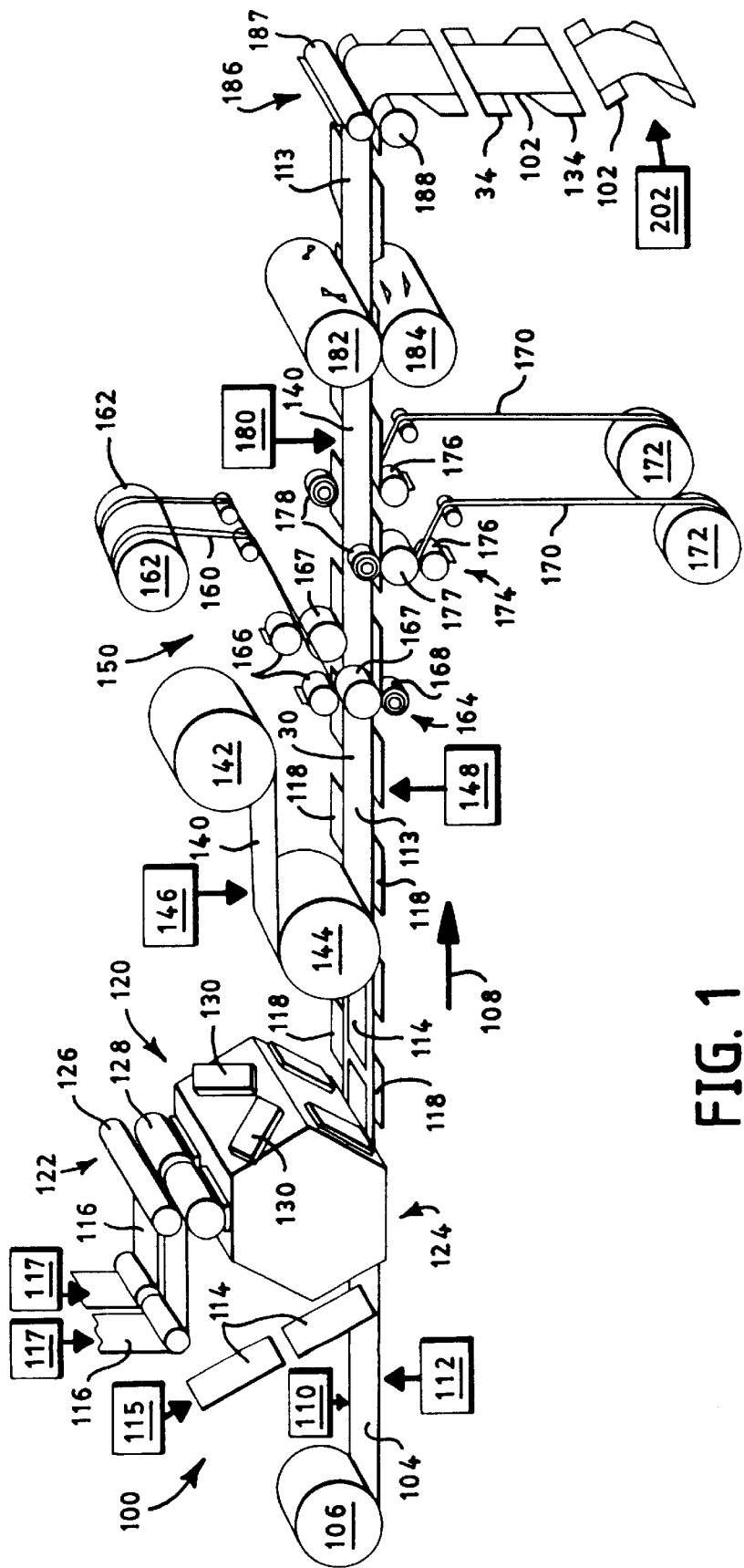
FIG. 1 is a schematic view of an exemplary embodiment of an assembly section for making garments such as training pants.
Figure 2:
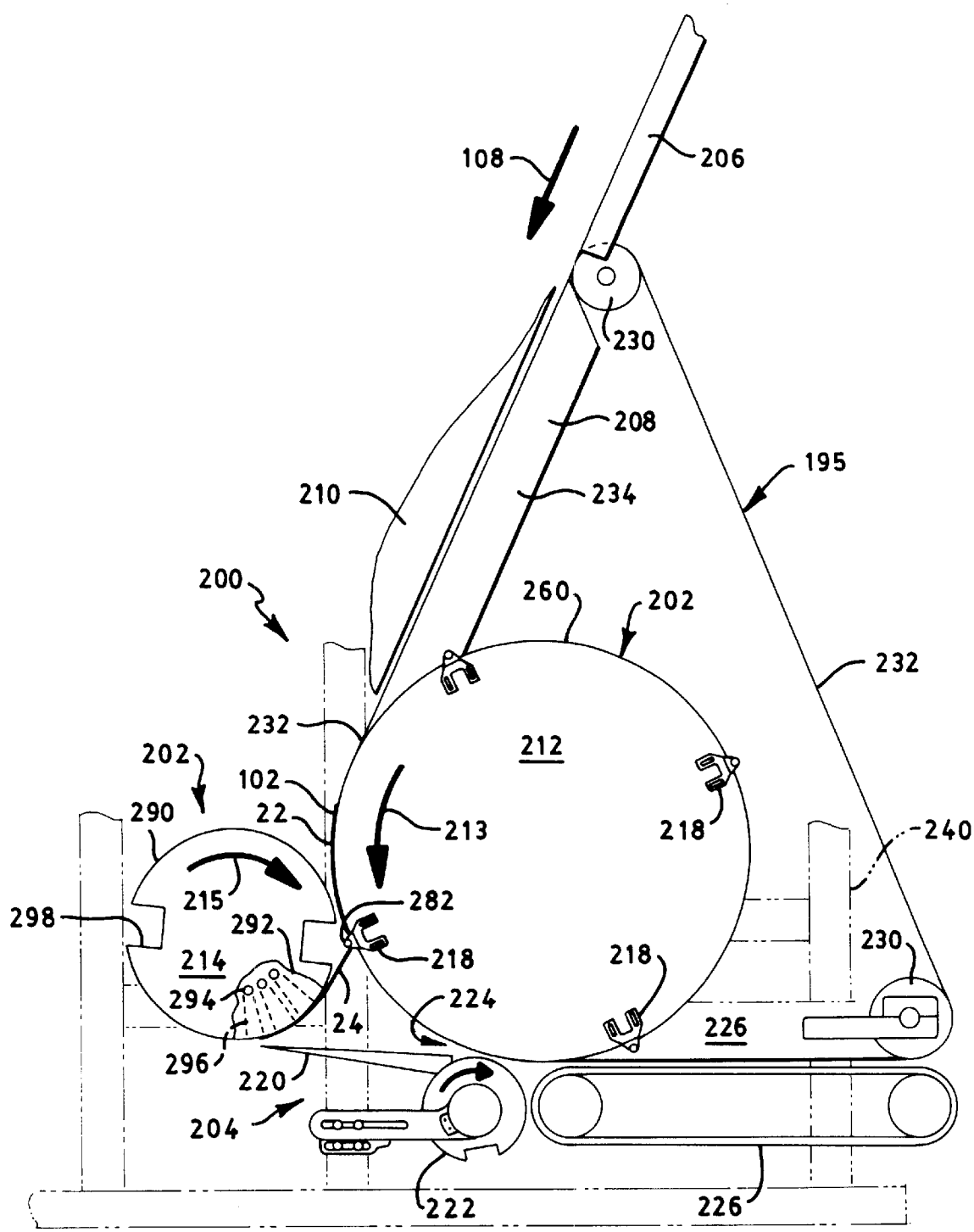
FIG. 2 is a schematic side view of an exemplary embodiment of a folding and seaming section for making garments such as training pants, with portions broken away for purposes of illustration, the folding and seaming section following the assembly section shown in FIG. 1.

FIGS. 1 and 2 representatively illustrate one embodiment of a method and apparatus for making a training pant 20. The training pant 20 is illustrated separately and in a partially fastened condition in FIG. 4. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 4:
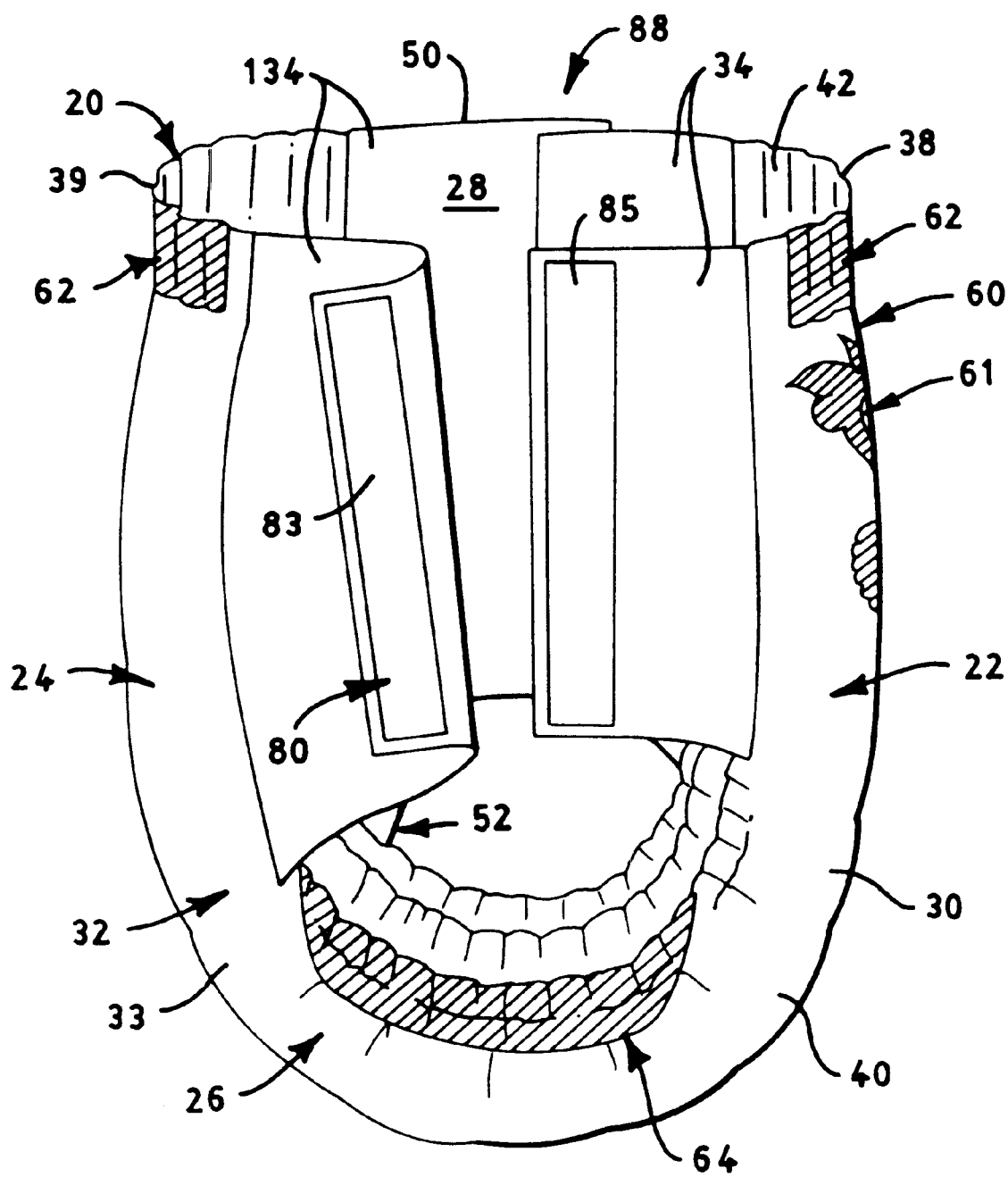
FIG. 4 illustrates a side view of a training pant made by the process and apparatus shown in FIGS. 1 and 2, where the fastening system is shown engaged on one side of the training pant and disengaged on the other side of the training pant.
Figure 5:
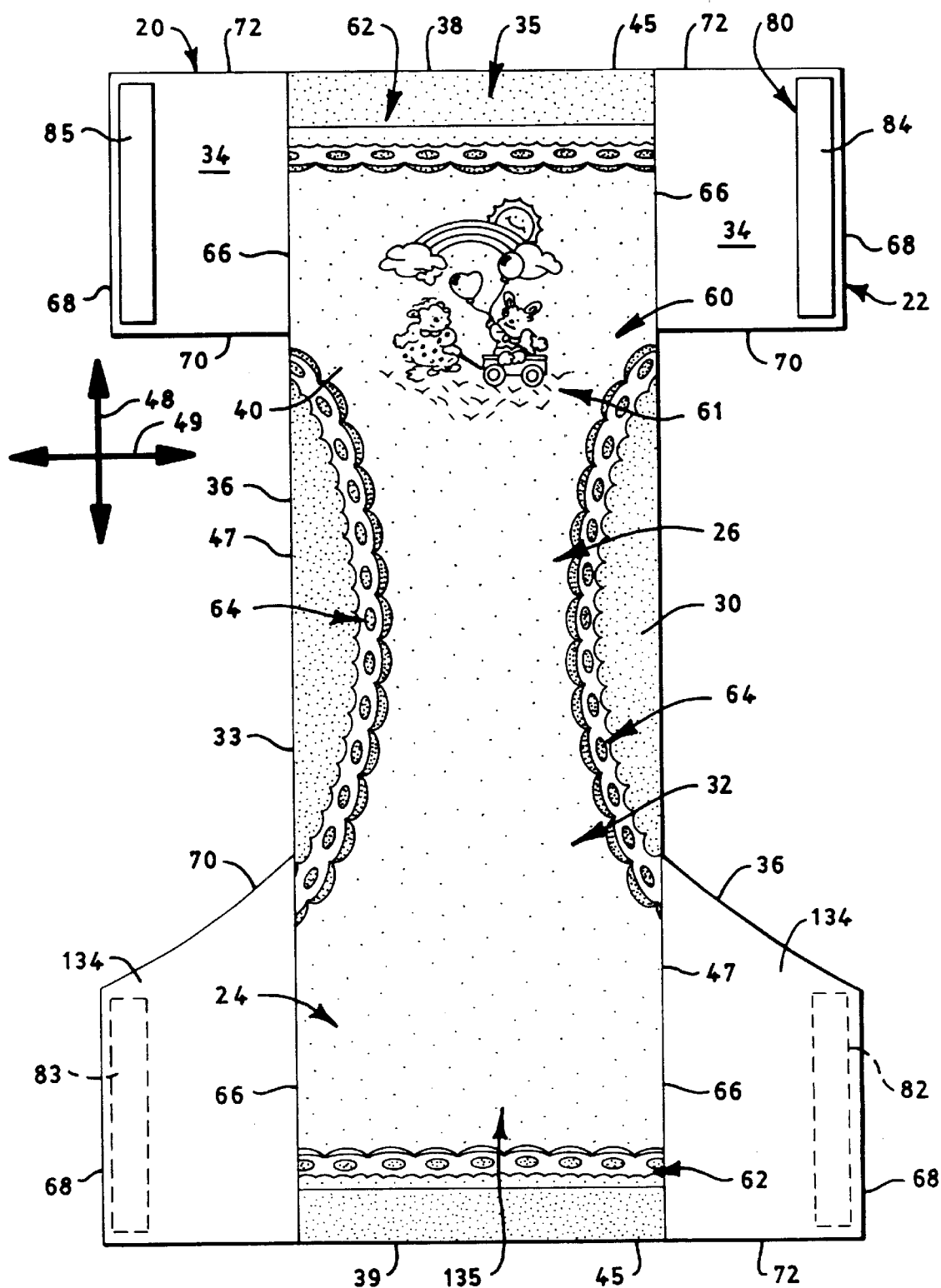
FIG. 5 illustrates a plan view of the training pant shown in FIG. 4 in an unfastened, stretched and laid flat condition, and showing the surface of the training pant that faces away from the wearer.
Figure 6:
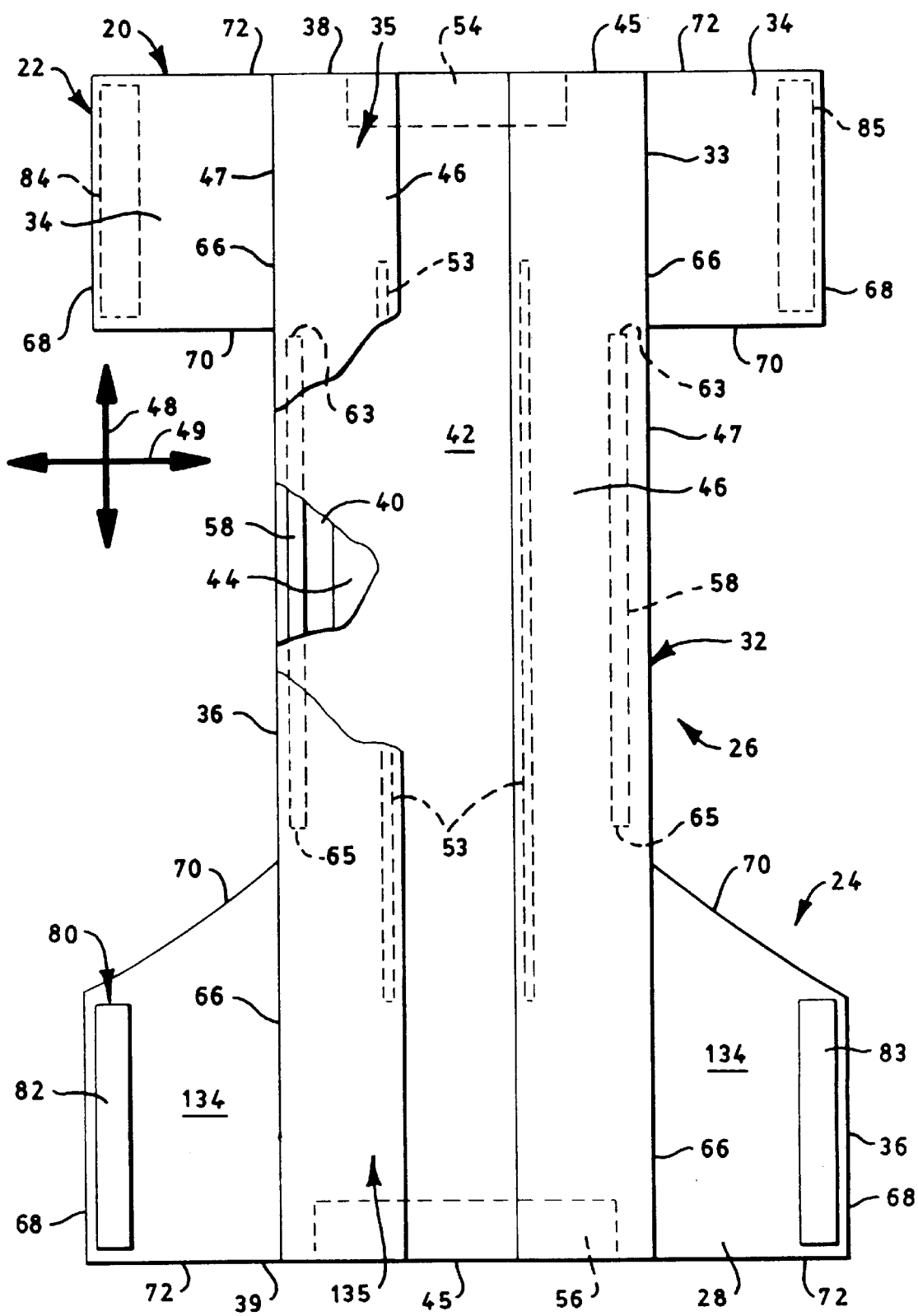
FIG. 6 illustrates a plan view similar to FIG. 5, but showing the surface of the training pant that faces the wearer when the training pant is worn, and with portions cut away to show the underlying features.

The illustrated absorbent chassis 32 comprises a composite structure 33 which can be rectangular or any other desired shape, a pair of transversely opposed front side panels 34, and a pair of transversely opposed back side panels 134. The composite structure 33 and side panels 34 and 134 may comprise two or more separate elements, as shown in FIG. 4, or be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pant. The illustrated composite structure 33 comprises an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The illustrated composite structure 33 has opposite linear end edges 45 that form portions of the front and back waist edges 38 and 39, and opposite linear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 6) can be operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 can be operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 4 and 5, the training pant 20 and in particular the outer cover 40 desirably comprise one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal center line of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pennsylvania in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pant can comprise elastomeric or nonelastomeric materials.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 5 and 6.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Alternatively, the fastening components can comprise interlocking similar surface fasteners; adhesive or cohesive fastening elements such as an adhesive fastener and an adhesive-receptive landing zone or material; or the like. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also comprise any fibrous structure capable of entangling or catching hook type materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82–85 are available from commercial vendors such as Velcro Industries B.V., Amsterdam, Netherlands or affiliates thereof, and are identified as Velcro HTH-829 with a unidirectional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 6, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 are located within about 2 centimeters, and more particularly within about 1 centimeter, of the distal edges 68, the waist end edges 72, and the leg end edges 70.

With particular reference to FIG. 5, the second fastening components 84 and 85 are desirably although not necessarily disposed on the outer surface 30 of the training pant 20 in the front waist region 22. The second fastening components 84 and 85 are sized to receive the first fastening components 82 and 83 and can be positioned along the distal edges 68 of the front side panels 34, and abutting or adjacent to the waist end edge 72. In certain embodiments, for example, the second fastening components 84 and 85 are located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks.

Figure 3:
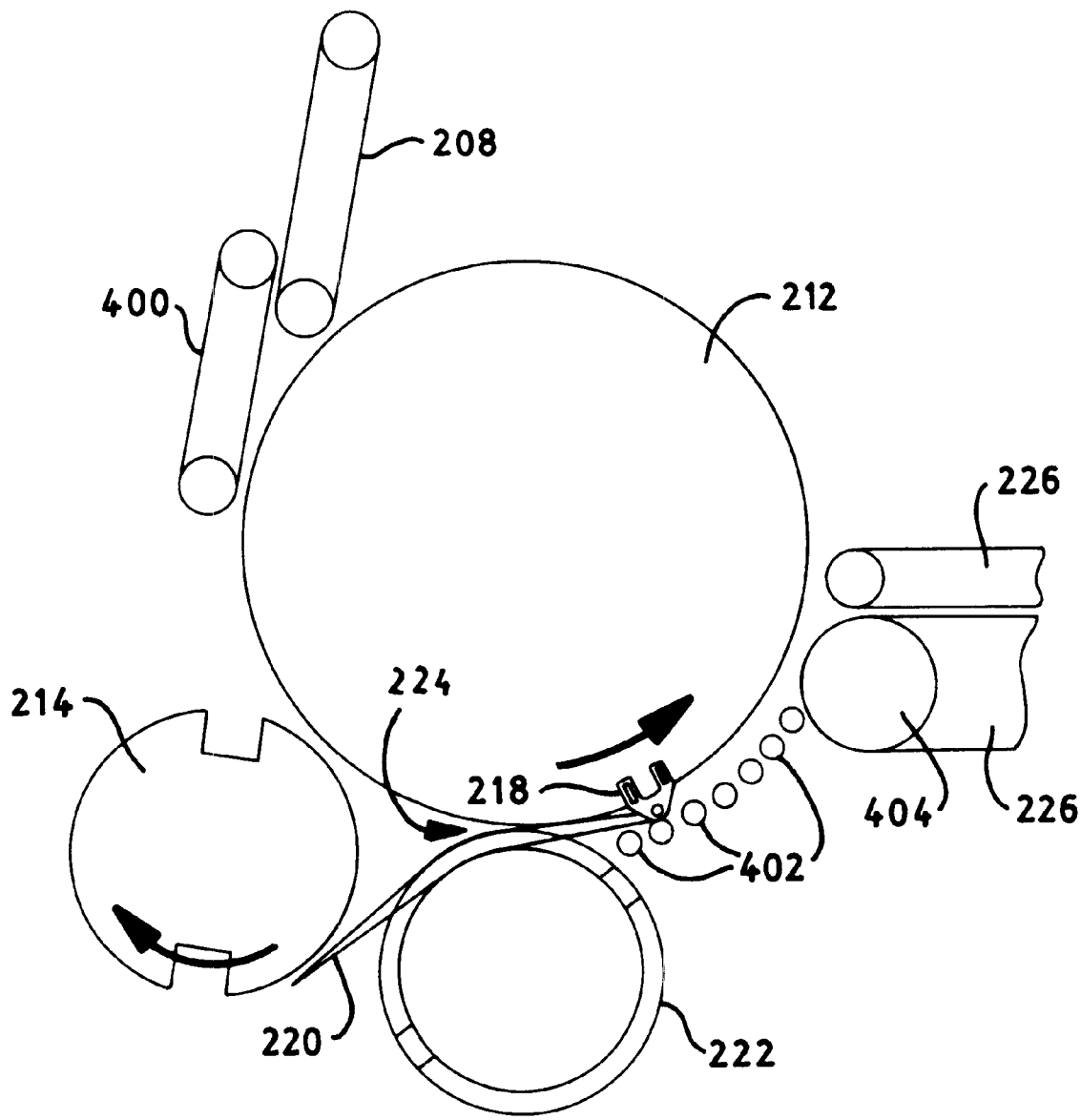
FIG. 3 is a schematic side view of an alternative embodiment of a folding and seaming section for making garments such as training pants.

The fastening components 82–85 can be adhered to the side panels 34 and 134 by any means known to those skilled in the art such as adhesive bonds, ultrasonic bonds or thermal bonds. The fastening components can comprise separate fastening elements or can comprise distinct regions of an integral material. For example, the training pant 20 can include an integral second fastening material disposed in the front waist region 22 for refastenably connecting to the first fastening components 82 and 83 at two or more different regions, which define the second fastening components 84 and 85 (FIG. 3). In a particular embodiment, the fastening components can comprise integral portions of the waist regions. For instance, one of the elastomeric front or back side panels can function as second fastening components in that they can comprise a material that is releasably engageable with fastening components disposed in the opposite waist region.

The fastening components are desirably rectangular, although they may alternatively be square, round, oval, curved or otherwise non-rectangularly shaped. In particular embodiments, each of the fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a lengthto-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it can be desirable in some embodiments for the front side panels 34 to be longitudinally spaced from the back side panels 134 (see FIGS. 5 and 6). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 4) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is measured parallel to the transverse axis 49 between the longitudinal center lines of the fasteners.

An exemplary embodiment of an assembly section 100 for making a continuous stream of partially assembled, discrete garments 102 is illustrated in FIG. 1. The specific equipment and processes used in the assembly section 100 can vary greatly depending on the specific type of garment being manufactured. The particular process and apparatus described in relation to FIG. 1 is specifically adapted to manufacture training pants 20 of the type illustrated in FIG. 4.

The various components of the training pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 1 and 2. Suitable absorbent supply mechanisms, web unwinds, conveyor systems, registration systems, drives systems, control systems and the like, for use with the present process are disclosed in U.S. Pat. No. 5,766,389 issued Jun. 16, 1998 to Brandon et al., which is incorporated herein by reference. Also, the outer cover graphics 61 are not shown in FIGS. 1, 2 and 7.

A continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each training pant. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 1 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pant 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and married with the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream of the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

The continuously moving product assemblage 113 next advances to a fastener application station 150 where fastening components 82–85 are bonded to the strips 118 of side panel material 116. The location of the fastening components on the composite is a function in part of the configuration of the assembly section 100. The illustrated assembly section 100 is configured so that the upwardly facing surface of the product assemblage 113 will become the outer surface 30 of the training pant 20 and the downwardly facing surface will become the inner surface 28. Moreover, the illustrated assembly section 100 is configured to produce partially assembled training pants 102 having the front waist region 22 of a leading garment connected to the back waist region 24 of a trailing garment. The process could alternatively employ any combination of different orientations. For example, the upwardly facing surface of the product assemblage could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 7:
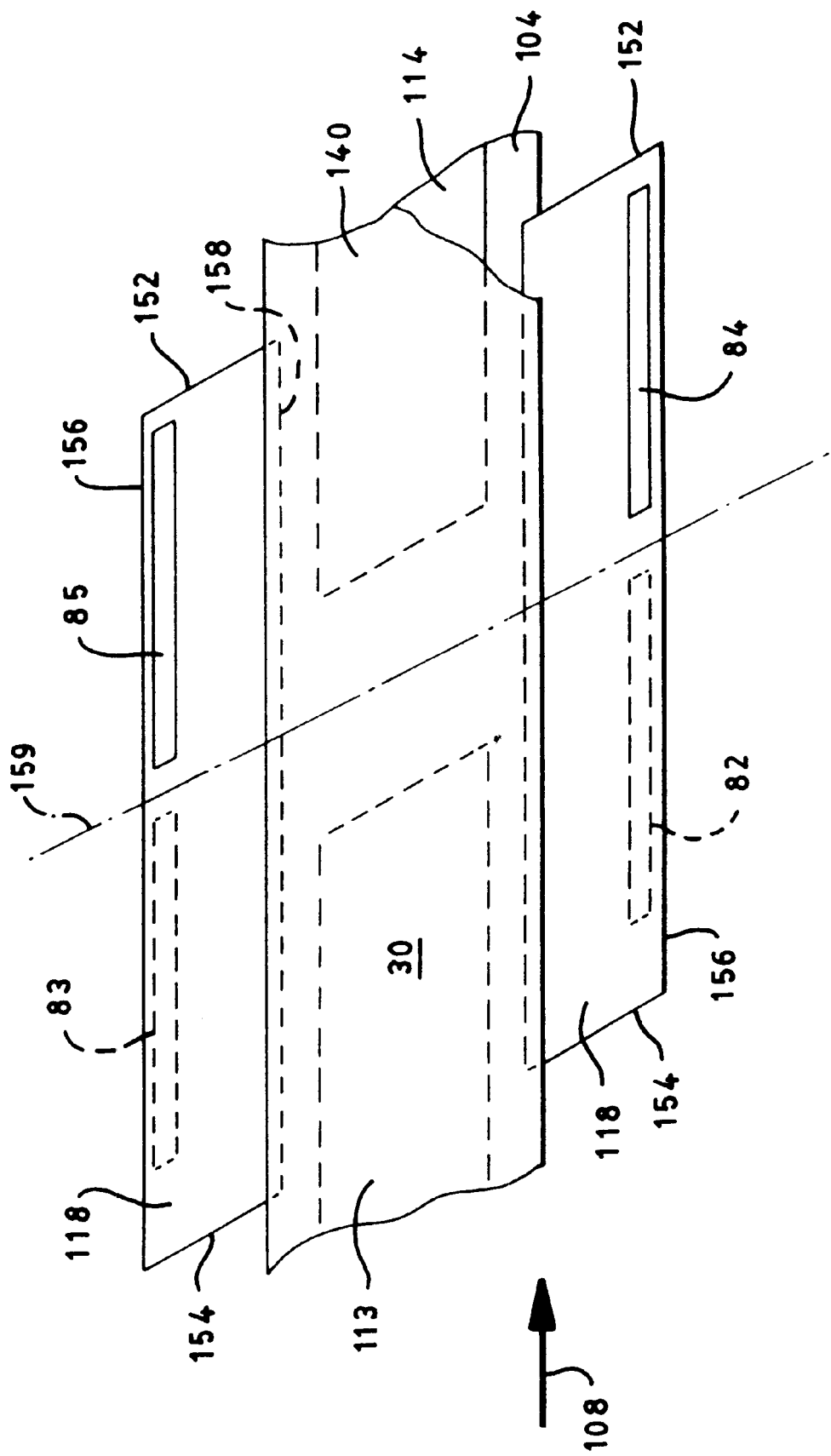
FIG. 7 illustrates a portion of a continuously moving assemblage at one point in the assembly section illustrated in FIG. 1.

The location of the fastening components 82–85 in this embodiment is best illustrated in FIG. 7, which shows a portion of the product assemblage 113 which is moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 102. Based on the illustrated orientation of the continuously moving product assemblage 113, the first fastening components 82 and 83 can be bonded to the underside of the strips 118 and the second fastening components 84 and 85 can be bonded to the top of the strips. Additionally, the first fastening components 82 and 83 can be disposed relatively closer to the trailing edge 154 and the second fastening components 84 and 85 can be disposed relatively closer to the leading edge 152. The first fastening components 82 and 83 can be spaced in the machine direction 108 from the second fastening components 84 and 85 so that the cut line 159 passes therebetween.

With reference again to FIG. 1, continuous webs of second fastener material 160 used to form the second fastening components 84 and 85 can be provided from supply rolls 162 or other suitable sources. The second fastener materials 160 can be cut into individual second fasteners 84 and 85 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 and 83 can be provided from supply rolls 172 or other suitable sources. The first fastener materials 170 can be cut into individual first fasteners 82 and 83 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

Other arrangements can be used to attach the fastening components 82–85. For example, the fastening components can be applied to the side panel material 116 prior to uniting the side panel material with the bodyside liner material 104 and/or the outer cover material 140; the fastening components can be applied to the bodyside liner material 104 and/or outer cover material 140, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites 82, 84 and 83, 85; or the like.

After the fastening components are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location, that is the transverse location, of the fastening components 82, 84 and 83, 85. Particular ultrasonic bond patterns comprising individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in U.S. Patent Application Serial No. unknown, filed on May 15, 2001 by J. D. Coenen et al. and titled "Methods For Making Garments With Fastening Components," which is incorporated herein by reference. For secure attachment, it may be desirable to attach the fastening components with both adhesive and thermal bonds. Suitable attachment adhesives are available from commercial vendors such as Findley Adhesive, Inc., Wauwatosa, Wis. U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82–85 and the side panel material 116 when the side panel material 116 reaches a particular machine direction 108 location. In one particular embodiment, the target areas correspond to portions of the fastening components 82–85 near the waist edges 38 and 39. The bonding devices 180 can be registered to provide a relatively higher degree of bonding which begins while disposed on one fastening component (such as 84 in FIG. 7), continues through the region where the product assemblage 113 will subsequently be cut (see cut line 159 in FIG. 7), and ends after being disposed on another fastening component (such as 82). Alternatively, the bonding devices 180 can destroy engaging elements of the fastening components 82–85 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 5 and 6).

To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled training pants moving in the direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels. The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

With reference to FIG. 2, a transport system 195 transports the continuous stream of discrete training pants 102 in the machine direction 108 to a folding and seaming station 200. In the illustrated embodiment, the folded training pants 102 are transported with the back waist region 24 leading the front waist region 22. For ease of explanation, the back waist region 24 will also be referred to as the leading half of the training pant 102 and the front waist region 22 will also be referred to as the trailing half of the training pant. Alternatively, the orientation could be reversed so that the front waist region 22 leads the back waist region 24. The folding and seaming station 200 comprises a folding mechanism 202 to fold the training pants 102 about a fold line which extends in a lateral direction through the crotch regions 26 of the training pants. Desirably, each discrete training pant 102 is consistently folded about the fold line such that the waist regions 22 and 24 are positioned in facing relationship with the front and back waist edges 38 and 39 aligned with each other. The folding and seaming station 200 also comprises a fastener engagement mechanism 204 to bond the side panels 34 and 134 together to form prefastened and refastenable pants 20.

The transport system 195 can include a final-cutoff discharge mechanism 206 which conveys the discrete, partially assembled training pants 102 to an entry conveyor 208. While on the entry conveyor 208, a side panel folding apparatus 210 can fold at least some of the side panels 34 and 134 of the training pants 102, and particularly the side panels on the trailing half. From the entry conveyor 208, the training pants 102 can be transferred to a main folding drum 212. As the training pants rotate with the main folding drum 212, the leading half 24 of each training pant 102 can be drawn onto the surface of a secondary folding drum 214. The main and secondary folding drums 212 and 214 are illustrated rotating in the direction of arrows 213 and 215, respectively. The trailing half 22 of each training pant 102 can remain under vacuum and can continue to rotate on the main folding drum 212. The folding mechanism 202 can be constructed such that the force maintaining the trailing half 22 on the main folding drum 212 is sufficient to draw the leading half 24 away from the secondary folding drum 214.

An auxiliary folding mechanism 218 can optionally be employed to ensure that the trailing half 22 remains on the main folding drum 212 and/or that the pants fold at a precise location in the crotch region 26. In the illustrated embodiment, the auxiliary folding mechanism 218 comprises a retractable pin mechanism. As the trailing half 22 continues to rotate on the main folding drum 212 and the leading half 24 is allowed to release from the secondary folding drum 214, the training pant 102 will assume a folded configuration with the crotch region 26 leading in the machine direction 108 and the waist regions 22 and 24 generally facing one another.

The fastener engagement device 204 can be employed at this point in the process to attach the fastening components 82–85 together. The embodiment illustrated in FIG. 2 employs a contouring mechanism comprising a contoured guide plate 220 and a contoured nip roll 222. The contoured guide plate and nip roll 220 and 222 can guide the side panels 134 on the leading half 24 to reposition the fastening components 82 and 83 on the leading half to correspond to the location of the fastening components 84 and 85 on the trailing half 22. The contoured nip roll 222 can be located in close proximity to the main folding drum 212 so that the fastening components 82–85 are forced into engagement as they pass through the nip 224 formed between the main folding drum and the contoured nip roll. Subsequently, exit conveyors 226 or other suitable means can be employed to transport the now-assembled training pants 20 to other stations for processing and/or packaging.

The illustrated transport system 195 can comprise a plurality of rotatable pulleys or rolls 230, a continuous belt 232 carried on the rolls, and a drive system (not shown) operatively connected to the rolls. The continuous belt 232, which defines a primary transport surface for the pants 102, can comprise a fluid-permeable material and can encircle the rolls 230 and main folding drum 212. The transport system 195 desirably transports the training pants 102 in a primary direction of movement with the longitudinal center line of the training pants traveling on the longitudinal center line of the transport system. Suitable conveyor mechanisms such as vacuum conveyors or nonvacuum conveyors are available from various commercial vendors.

Figure 8:
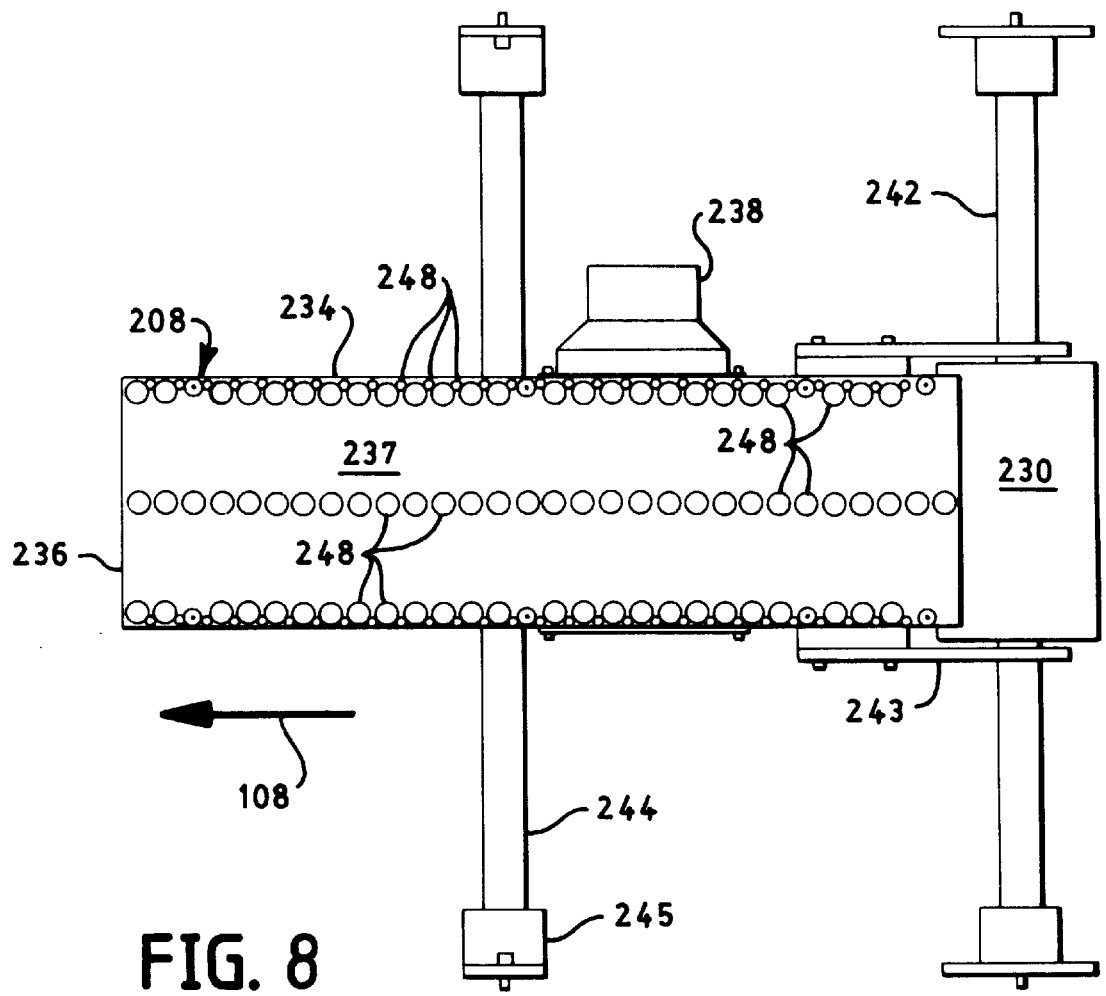
FIGS. 8 and 9 illustrate top and side views respectively of an entry vacuum box of the folding and seaming section shown in FIG. 2.
Figure 9:
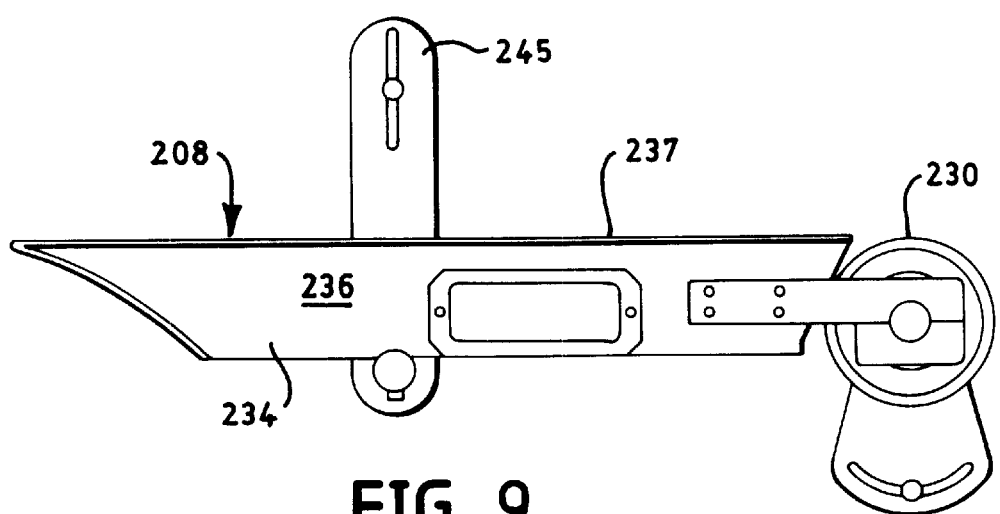

The entry conveyor 208 can include an entry vacuum box 234, which is separately illustrated in FIGS. 8 and 9. The entry vacuum box 234 can comprise a frame 236, a vacuum cover plate 237 attached to the frame with suitable fasteners, and a duct 238 for operatively connecting the chamber formed within the vacuum box to a source of vacuum. The vacuum box 234 can be mounted on any suitable support structure 240 (FIG. 2) by any means. In the illustrated embodiment, the entry vacuum box 234 can be connected by brackets 243 to a shaft 242 upon which a transport roll 230 is mounted, and connected by a suitable mounting shaft 244 and mounting brackets 245 to the support structure 240.

To facilitate folding of the side panels, the entry vacuum box 234 can have a width dimension perpendicular to the machine direction 108 that is less than the transverse width of the training pant 102. In particular, the width of the entry vacuum box 234 can be selected to be approximately equal to or less than the distance between the second fastening components 84 and 85 measured parallel to the transverse axis 49. The vacuum cover plate 237 suitably includes a plurality of apertures 248 or the like to draw the training pant 102 to the continuous vacuum belt 232. As illustrated in FIG. 8, the apertures 248 in the vacuum cover plate 237 can be nonuniformly arranged to provide differential vacuum in the cross-machine direction. More particularly, a plurality of apertures 248 can be located near the laterally outward portions of the vacuum cover plate 237 adjacent the side edges of the frame 236. With additional reference to FIGS. 10 and 11, the side edges of the frame 236 can be tapered to obtain vacuum pressure near the side edges of the vacuum box 234. A relatively lower concentration of open areas can occur in the central region of the vacuum box 234 to hold the absorbent chassis 32 of the training pant 102 on the continuous belt 232.

The side panel folding apparatus 210 can comprise any suitable mechanism for inwardly folding the side panels 34 of the trailing half 22 so that the second fastening components 84 and 85 are inverted. More particularly, the second fastening components 84 and 85 can initially be disposed on the outer surface 30 of the training pant 102 that faces the continuous belt 232. The side panel folding apparatus 210 can fold the laterally outward portions of the side panels 34 in the trailing half 22 so that the second fastening components 84 and 85 are directed away from the continuous belt 232. As illustrated, the side panel folding apparatus 210 can comprise helical skis 250 to fold the side panels 34 and second fastening components 84 and 85 inward 180 degrees toward the inner surface 28 and the center line of the entry conveyor 208. The garments could of course be folded in a reverse orientation, that is inside out, and subsequently reversed for use. The side panel folding apparatus 210 can be mounted on the entry conveyor 208, the support structure 240, partially or fully on the main folding drum 212, or the like.

Figure 10:
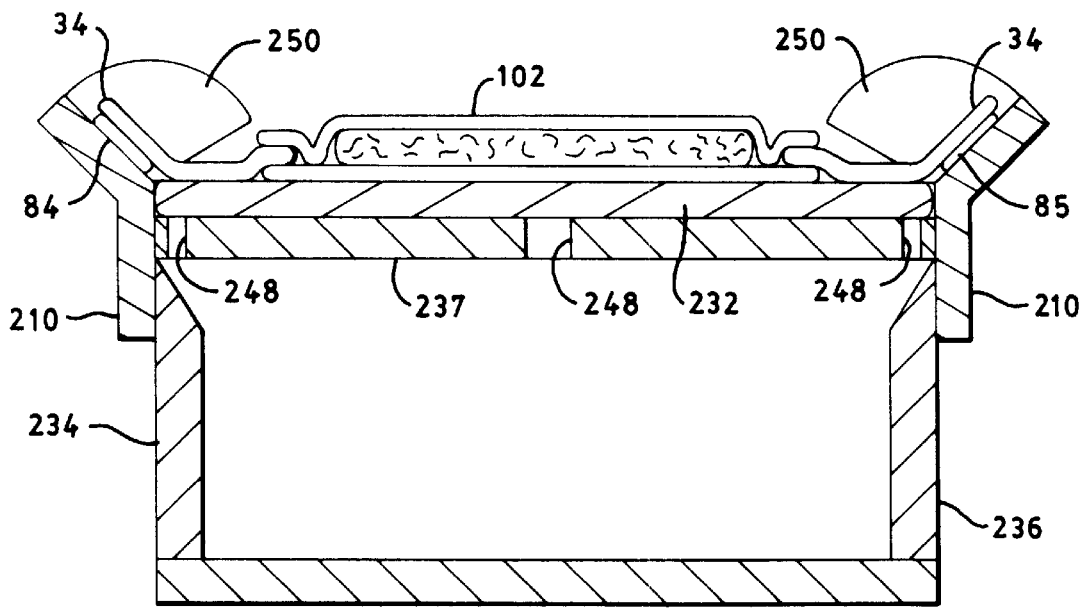
FIGS. 10 and 11 illustrate section views of a portion of a training pant at a series of positions between the entry vacuum box and a side panel folding apparatus of the folding and seaming section shown in FIG. 2.
Figure 11:
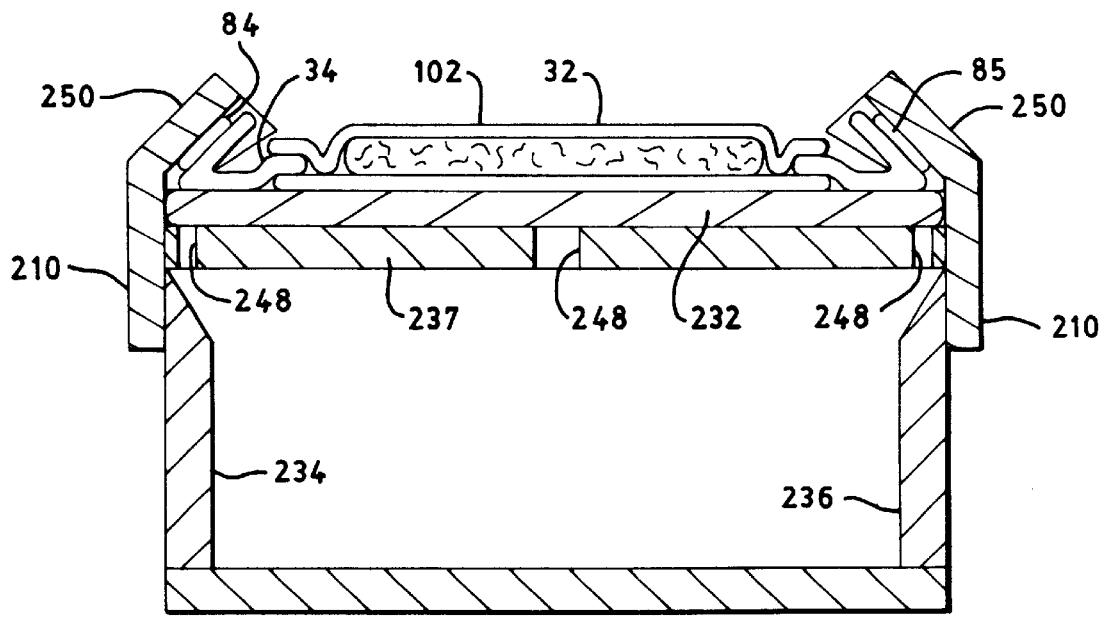

FIGS. 10 and 11 illustrate section views of a training pant 102 at two positions along the entry conveyor 208 where the side panel folding apparatus 210 inwardly folds the second fastening components 84 and 85. In FIG. 10 the laterally outward portions of the side panels 34 are beginning to crease at a location adjacent inward edges of the second fastening components 84 and 85. A relatively high level of vacuum adjacent the folding skis 250 can facilitate formation of a tighter crease for folding. In one particular embodiment, for example, the width of the training pant 102 measured parallel to the transverse axis 49 can be about 25 centimeters, and the distance between the folding skis 250 can be about 20 centimeters. The folding skis 250 can continue to converge inward as the product moves downstream to the position illustrated in FIG. 11. At this point, the second fastening components 84 and 85 have been folded more than 90 degrees and can continue to be folded through 180 degrees where they will face away from the continuous belt 232. The second fastening components 84 and 85 can be maintained in an inwardly folded position by vacuum through the fluid-permeable side panels 134, or by other suitable means.

The side panel folding apparatus 210 can alternatively comprise other mechanisms for inwardly folding the side panels 34. For example, the side-panel folding apparatus 210 can comprise fluid nozzles to blow the lateral portions of the side panels inward. In the illustrated embodiment, the folding skis 250 inwardly fold the lateral portions of both the front and backside panels 34 and 134, although in particular embodiments the backside panels 134 are blown back to an unfolded configuration with a timed air blast. Alternatively, the side-panel folding apparatus 250 can comprise a timed or intermittent mechanism, for example, a timed fluid blast, which can inwardly fold only the lateral portions of the side panels in the trailing half of the training pant 102.

Figure 12:
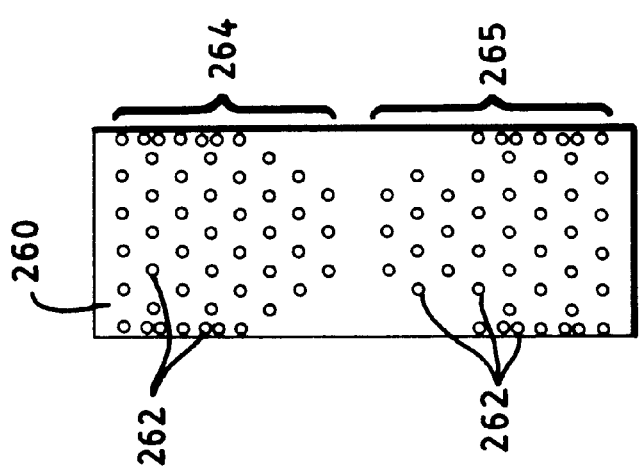
FIG. 12 illustrates a plan view of a portion of a main drum surface of a main folding drum shown in FIG. 2.

The training pant 102 can continue on the transport system 195 to the main folding drum 212. The main folding drum 212 can comprise a vacuum drum mounted on a shaft (not shown) and rotated by a suitable drive mechanism (not shown). The main folding drum 212 can include a main drum surface 260 comprising a pattern of apertures 262 (FIG. 12) for drawing the training pant 102 onto the continuous belt 232 as the training pant passes over the main drum surface. The main drum surface 260 can comprise a single pattern of apertures 262 configured to maintain one training pant on the drum surface or a plurality of repeating patterns of apertures, for example, four products per revolution. As illustrated by the single pattern of apertures 262 shown in FIG. 12, each pattern can be shaped to generally correspond to the shape of the training pant 102. The width of the drum can be the same as the cross-machine direction width of the entry conveyor 208. Further, each pattern can comprise a leading aperture zone 264 and a trailing aperture zone 265 which correspond to the leading and trailing halves 24 and 22 of the training pant 102. The transport system 195 and main folding drum 212 can be timed so that the positions of the leading and trailing halves 24 and 22 of each training pant 102 correspond to the locations of the leading and trailing aperture zones 264 and 265, respectively, on the main drum surface 260. As one alternative to vacuum holes drilled in the drum, the main folding drum 212 can comprise an open drum with vacuum plates and holes in the vacuum plates to match the pattern of the pant (not shown).

Figure 13:
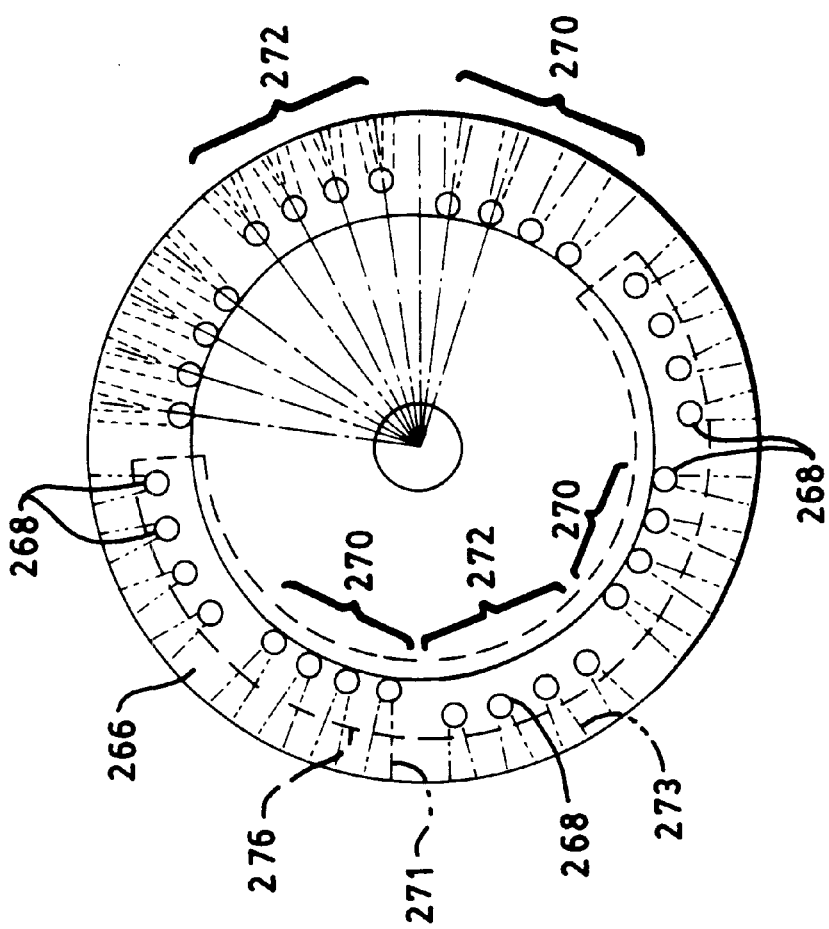
FIG. 13 illustrates a plan view of a sidewall of the main folding drum.

With reference to FIG. 13, the main folding drum 212 can comprise a sidewall 266 having formed therein a plurality of vacuum ports 268 in the form of lateral through holes. In the illustrated embodiment, the vacuum ports 268 define a plurality of radially inner sets of vacuum ports 270 and a plurality of radially outer sets of vacuum ports 272. The radially inner sets of vacuum ports 270 can be operatively associated with the apertures 262 forming the leading aperture zones 264, for example, by a plurality of channels 271 connecting the radially inner set of ports with the leading aperture zones. Similarly, the radially outer sets of vacuum ports 272 can be operatively associated with the apertures 262 forming the trailing aperture zones 265, for example by channels 273. Alternatively, of course, other configurations or devices can be used to provide separate vacuum control of the leading and trailing halves 24 and 22 of the training pant 102. For example, the association of the radially inner and outer vacuum ports 270 and 272 can be reversed relative to the leading and trailing aperture zones 264 and 265, or other configurations can be used.

Figure 14:
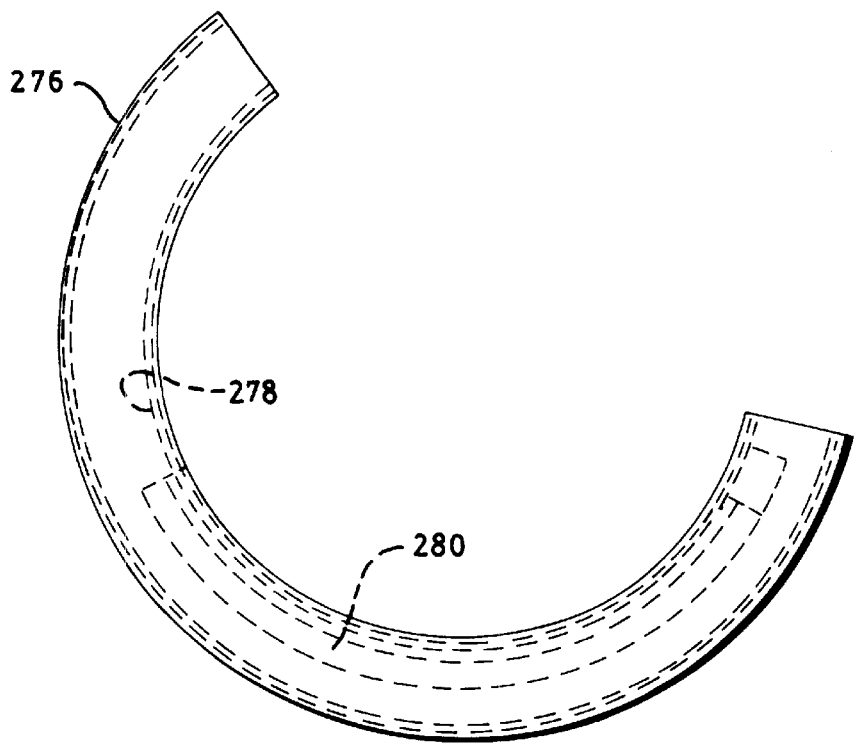
FIG. 14 illustrates a plan view of a vacuum shoe which can be used in combination with the main folding drum.

The main folding drum 212 can be operatively associated with a vacuum shoe 276, an example of which is depicted in FIG. 14. The vacuum shoe 276 can sealingly engage with the main folding drum sidewall 266 and permit rotational movement of the drum 212 relative to the vacuum shoe. The vacuum shoe 276 can be operatively connected to a vacuum source (not shown) and include a plurality of slots 278 for operatively connecting the radially inner and outer sets of vacuum ports 270 and 272 to the vacuum source. As illustrated, an interference plate 280 can be adjustably mounted within the vacuum shoe 276 to block communication between the radially inner set of vacuum ports 270 and the vacuum source. Alternatively, the interference plate 280 can comprise an integral portion of the vacuum shoe 276. Further, the interference plate 280 could alternatively block the radially outer set of vacuum ports 272 which could be ported to the leading half of the pant.

In operation, the leading half 24 of each training pant 102 can be disposed on a leading aperture zone 264 as the training pants are transferred from the entry conveyor 208 to the main drum surface 260. As the main drum 212 is rotated in the direction of arrow 213, the trailing half 22 can then be disposed on the trailing aperture zone 265. The main folding drum 212 and the vacuum shoe 276 can be configured so that the leading and trailing halves 24 and 22 are both under vacuum as the training pant 102 is transferred onto the main drum surface 260.

Figure 15:
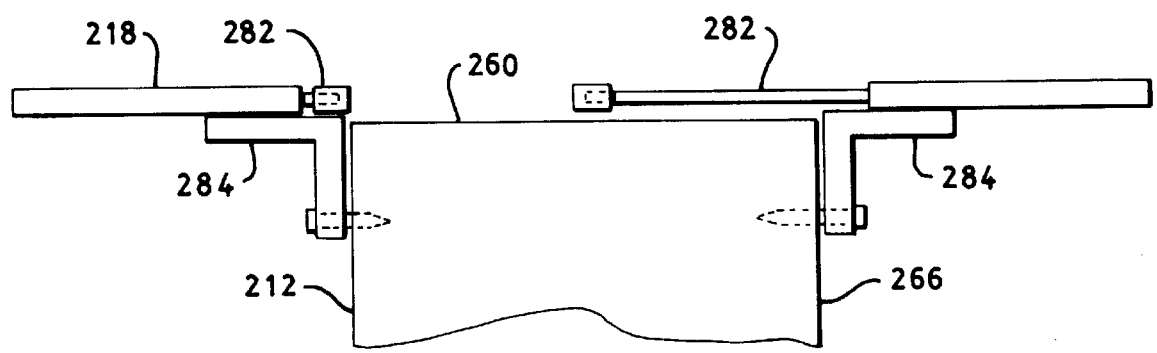
FIG. 15 schematically illustrates a retractable pin mechanism which can be employed in the folding and seaming section shown in FIG. 2.

The auxiliary folding mechanism 218 (FIGS. 2, 15 and 16) can optionally be employed to assist with folding of the training pants 102. In one embodiment, the auxiliary folding mechanism 218 comprises a retractable pin mechanism including one or more opposed pairs of retractable pins 282. The pins 282 can be mounted on the main folding drum sidewalls 266, for example, at positions between the leading and trailing aperture zones 264 and 265 to correspond with the crotch region 26 of each training pant. While retracted, the opposed pair of pins 282 can be located axially outward from the training pant 102, at least in the crotch region 26. Conversely, while extended, the opposed pair of pins 282 can be aligned and positioned in close proximity to one another. As shown in FIG. 15, the pins 282 can be mounted with brackets 284 or other suitable means at a position slightly above the main drum surface 260 so that the training pant 102 can be sandwiched between the pins and the main drum surface when the pins are extended. The opposed pair of pins 282 can be timed to extend and retract in unison, although for purposes of illustration one pin is shown in an extended position and the opposed pin is shown in a retracted position in FIG. 15. The main folding drum 212 can have one opposed pair of pins 282 for each product per drum revolution. The pins 282 can be formed of stainless steel, aluminum, or other suitable low-friction materials. In an alternative embodiment, the pins and pin movement mechanism can be internal to the main folding drum (not shown). Such an embodiment could allow for much shorter pin movement only in the crotch region of the pant. In another alternative embodiment, a concentrated vacuum region can be employed in the crotch region 26 of the training pant, thus forming an alternative auxiliary folding mechanism 218.

The secondary folding drum 214 (FIGS. 2 and 16) can comprise a vacuum drum rotatively mounted to the support structure 240. The secondary folding drum 214 can be operatively connected to the drive mechanism for the main folding drum 212 or be driven from an independent drive mechanism to rotate in the direction of arrow 215. The secondary folding drum 214 can comprise a curved outer surface 290 formed with a plurality of apertures (not shown). The secondary folding drum 214 can also comprise a sidewall 292 having a plurality of vacuum ports 294 that are in fluid communication with the apertures of the curved outer surface 290, for example via channels 296 (FIG. 2). A vacuum shoe (not shown) can be sealingly connected to the sidewall 292 to operatively connect the vacuum ports 294 to a source of vacuum (not shown). In the illustrated embodiment comprising a retractable pin mechanism 218, the secondary folding drum 214 can also comprise one or more recessed portions 298 formed in the outer surface 290 and sidewalls 292 to provide space for the pins 282 to pass between the main and secondary folding drums 212 and 214. The secondary folding drum 214 could also be in the form of one or more vacuum pucks (not shown). The secondary folding drum 214 can be positioned in close proximity to the main folding drum 212, for example, separated by the thickness of the unfolded training pant 102. The secondary folding drum 214 can be sized to accommodate two products per revolution as illustrated, or can be sized to accommodate any number of products per revolution.

The vacuum shoe for the secondary folding drum 214 can be configured to supply vacuum to the apertures only when the leading half 24 of the training pant 102 is positioned on the secondary folding drum, which position is illustrated in FIG. 2. The main and secondary folding drums 212 and 214 can be operated at the same or different levels of vacuum. The secondary folding drum 214 can have any suitable width, for example, a width corresponding to the width of the training pant 102 such that the side panels 134 of the leading half 24 of the training pant will be drawn to the outer surface 290 of the secondary folding drum 214 over the full width of the pant. The secondary folding drum outer surface 290 can be formed of any material that permits slippage of the training pant 102 as described hereinafter, for example, formed of nylon, or the like.

At the point where the leading half 24 of the training pant 102 reaches the tangent point between the main and secondary folding drums 212 and 214, vacuum to the leading aperture zone 264 on the main drum surface 260 can be interrupted. With reference again to FIGS. 13 and 14, the tangent point between the main and secondary folding drums 212 and 214 can signify the point where the radially inner set of vacuum ports 270 associated with a given training pant are no longer in fluid communication with the vacuum source due to the position of the interference plate 280 within the vacuum shoe 276. The radial position of the interference plate 280 can be set to coincide with the radially inner sets of vacuum ports 270, such that the radially outer sets of vacuum ports 272 associated with the trailing aperture zone 265 remain in fluid communication with the vacuum source. Depending on process conditions such as speed and levels of vacuum, it may be beneficial to interrupt communication between the leading aperture zone 264 and the vacuum source somewhat before the tangent point. At or before the leading half 24 of the training pant 102 reaches the tangent point between the main and secondary folding drums 212 and 214, vacuum can be applied to the secondary folding drum outer surface 290. Consequently, as the leading half 24 of the training pant 102 passes through the tangent point, the leading half will be transferred from the main folding drum 212 to the secondary folding drum 214. For purposes of the present invention, the "tangent point" will refer to the location of minimum gap between the main and secondary folding drums.

For subsequent operations, it is desirable that the side panels 134 of the leading half not be folded. Thus, the leading side panels can either not be folded to this point or can be unfolded prior to such subsequent operations. The side panels 134 of the leading half 24 can be unfolded by themselves upon transfer to the secondary folding drum 214 or can be assisted by a fluid source from a nozzle or the like (not shown). Such fluid assist can be timed with the location of the side panels on the leading half 24.

The auxiliary folding mechanism 218 can be activated at any point after the crotch region 26 of the training pant 102 is transferred from the entry conveyor 208 to the main folding drum 212. Desirably, the auxiliary folding mechanism 218 is fully activated, that is extended, when the crotch region 26 of the training pant 102 reaches the tangent point between the main and secondary folding drums 212 and 214. The auxiliary folding mechanism 218 can be controlled and activated by any suitable means. In one particular embodiment, the auxiliary folding mechanism 218 can comprise a cam system having a cam follower mounted on the main drum and operatively connected to the pins, and a cam mounted on the support structure and disposed adjacent the rotating main folding drum, such that the cam follower repeatedly extends and retracts the pins. Alternatively, the auxiliary folding mechanism 218 can comprise a pneumatic system, such as pneumatic cylinders operatively connected to extend and retract the pins, a feeding air supply inside a main shaft of the main folding drum 212, and air couplings at multiple locations to connect the pneumatic cylinder to the air supply within the main shaft.

After the crotch region 26 and the retractable pins 282 pass through the tangent point, vacuum can be maintained on the trailing half 22 of the training pant 102. The trailing half 22 can thus remain on the continuous belt 232 and rotate on the main folding drum 212 in the direction of arrow 213. The leading half 24 of the training pant 102 will be allowed to slip on the secondary folding drum outer surface 290 whereupon the training pant will assume a folded configuration. In effect, the leading half 24 is temporarily diverted from the transport system 195 and its primary direction of movement onto the secondary folding drum 214 and its divergent secondary direction of movement. The crotch region 26 and trailing half 22 continue along the primary direction of movement and pull the leading half 24 from the secondary folding drum 214, thus reestablishing movement of the leading half in the primary direction of movement. Vacuum can be maintained on the secondary folding drum outer surface 290, as slippage of the leading half 24 will expose apertures in the outer surface to atmosphere and release the vacuum hold on the leading half. Alternatively, the vacuum can be disengaged on the secondary folding drum 214 after the crotch region 26 passes through the tangent point of the main and secondary folding drums 212 and 214.

The retractable pin mechanism 218 can assist in providing a folding line through the crotch region 26 that is perpendicular to the machine center line and located intermediate the front and back waist edges 38 and 39 of the training pant 102. The angular position of the secondary folding drum recessed portions 298 can be timed with the angular position of the retractable pins 282. The retractable pin mechanism 218 can be maintained in an extended position until the pins 282 pass the contoured nip roll 222.

Figure 16:
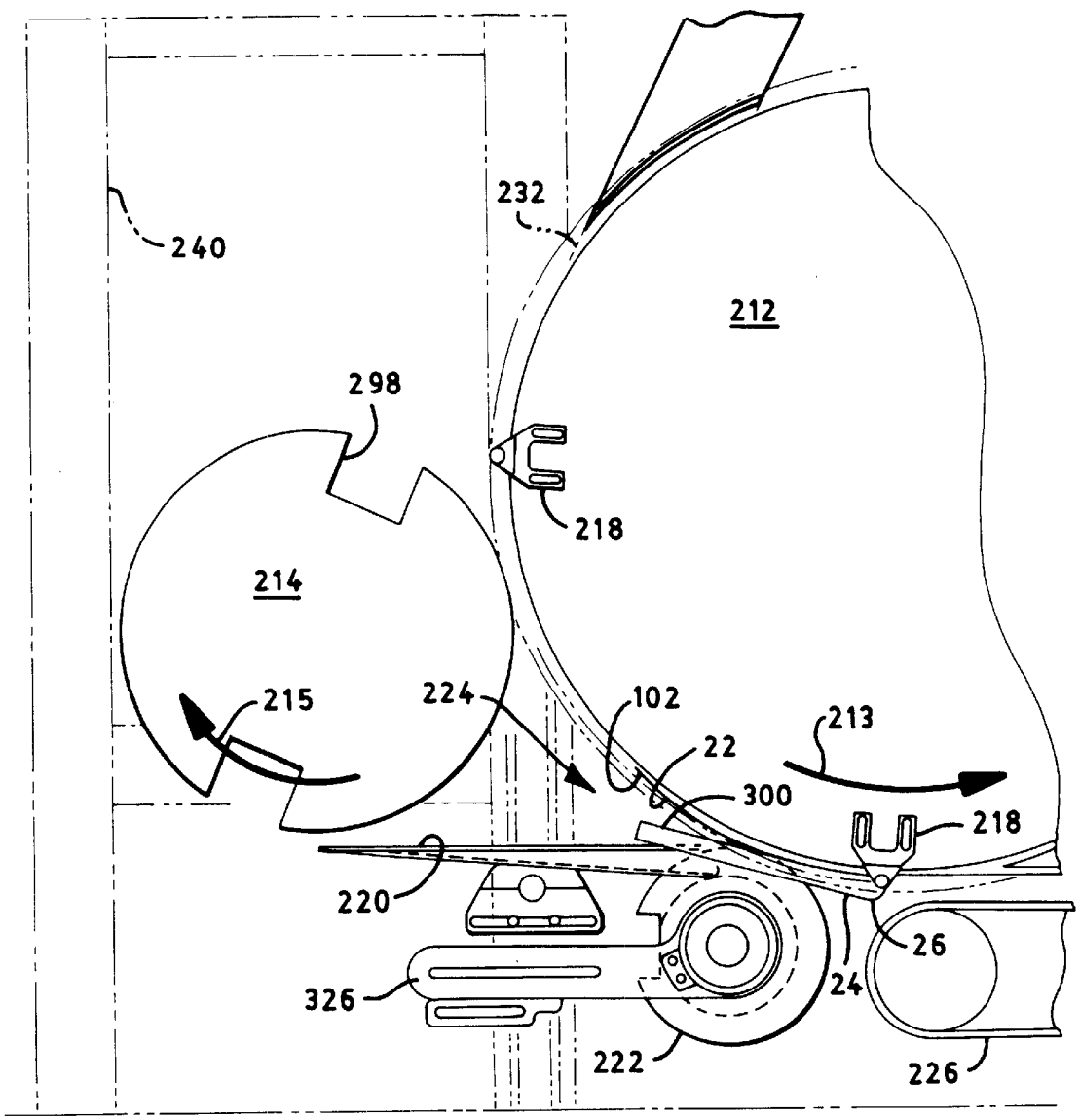
FIG. 16 illustrates an enlarged side view of the folding and seaming section shown in FIG. 2, depicting the position of a training pant in a fastener engagement mechanism.

FIG. 16 illustrates a training pant 102 at a location downstream of the location illustrated in FIG. 2. The trailing half 22 of the training pant 102 remains disposed on the continuous belt 232 in close association with the main folding drum 212. The crotch region 26 of the pant remains supported against the conveyor belt 232 by the retractable pin mechanism 218. The leading half 24 of the training pant 102, at this point, is following the crotch region 26. The position of the lateral portions of the back side panels 134 of the leading half 24 are denoted at reference numeral 300 in FIG. 16. Components of the fastener engagement device are separately illustrated in FIGS. 17–21.

Figure 18:
FIGS. 17 and 18 illustrate side and top views of a contoured guide plate of the fastener engagement mechanism shown in FIG. 16.
Figure 17:
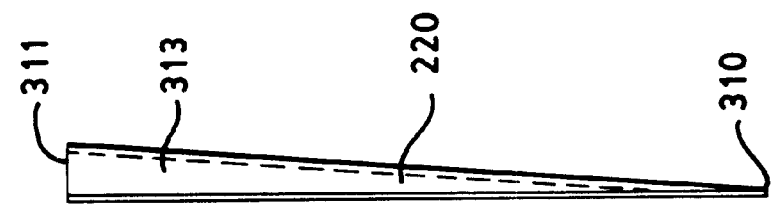

The contoured guide plate 220 can be positioned between the secondary folding drum 214 and the contoured nip roll 222 such that the leading half 24 comes in contact with and slides across a surface of the contoured guide plate as the training pant 102 advances toward the contoured nip roll. With reference to FIGS. 17 and 18, the contoured guide plate 220 comprises an upstream edge 310, an opposite downstream edge 311, a central section 312 extending between the upstream and downstream edges, a pair of triangularly shaped sidewalls 313 on either side of the central section, and a pair of flanges 314 outward of the sidewalls. The central section 312 and flanges 314 can reside in a common plane adjacent the upstream edge 310. The angled sidewalls 313 can provide vertical separation between the plane containing the central section 312 and the plane containing the flanges 314 moving toward the downstream edge 311. The contoured guide plate 220 can be mounted on the support structure 240 downstream from the secondary folding drum 214, but sufficiently close so that the leading half 24 can contact the guide plate. The guide plate 220 can be formed of stainless steel, aluminum, other low friction materials, or the like.

Use of the terms "vertical" and "horizontal" and variations thereof have their usual meaning, however, the present invention contemplates that vertical surfaces can be "generally vertically" disposed if desired and would thus be oriented between the true vertical position and about a 45 degree position relative to the true vertical position. The same interpretation for "generally horizontally" disposed means an orientation between the true horizontal and about a 45 degree position relative thereto. The terms "upper" and "lower" are provided for ease of understanding, and it should be recognized that the spatial arrangement of the elements being described could be inverted or arranged in another manner.

Figure 21:
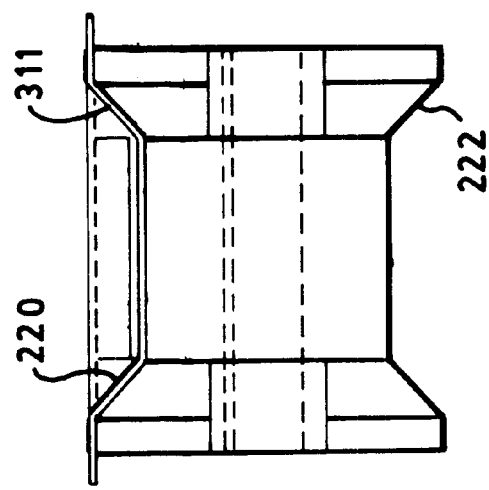
FIG. 21 illustrates a position the contoured guide plate and nip roll can assume relative to one another in the fastener engagement mechanism.
Figures 19, 20:
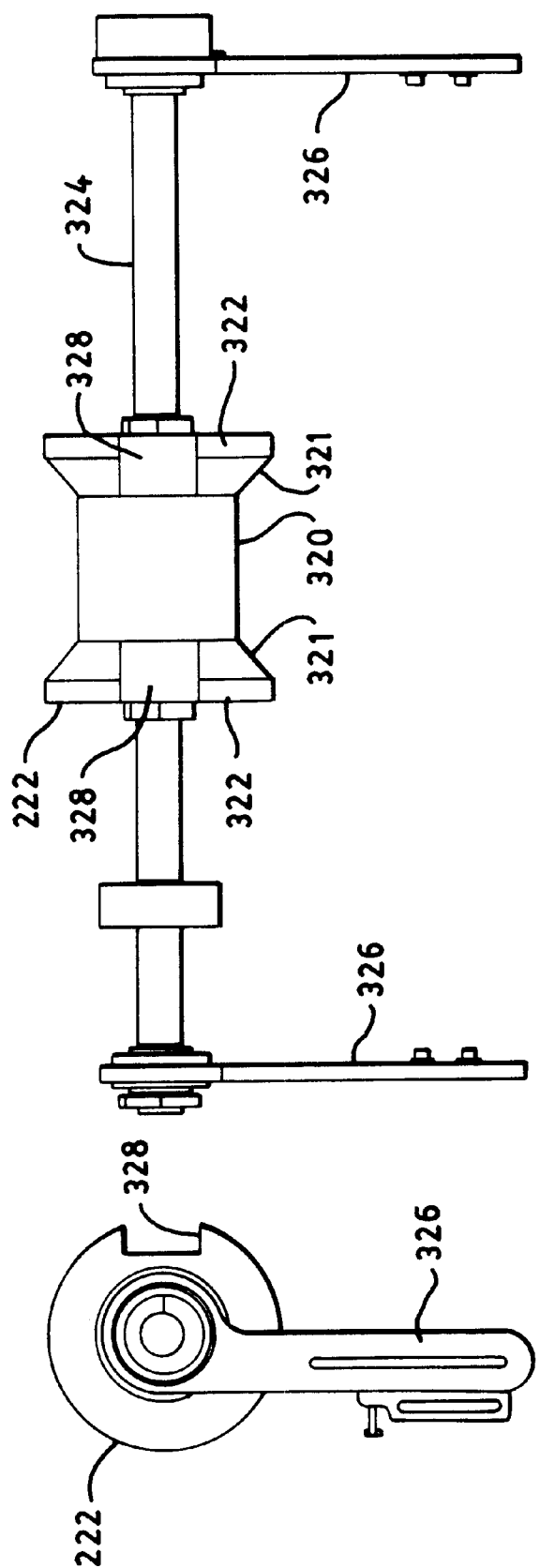
FIGS. 19 and 20 illustrate side and top views of a contoured nip roll of the fastener engagement mechanism shown in FIG. 16.

With reference to FIG. 19 and 20, the contoured nip roll 222 can have an axial profile similar to the profile of the contoured guide plate 220 adjacent its downstream edge 311. In particular, the contoured nip roll 222 can comprise a generally flat central section 320, a pair of angled sidewalls 321 outward from the central section, and flanges 322 outward from the angled sidewalls. The diameter of the contoured nip roll 222 can increase from the central section 320 axially outward to each flange 322. As shown in FIG. 21, the downstream edge 311 of the contoured guide plate 220 can be aligned with and positioned in close proximity to the contoured nip roll 222 so that the leading half 24 of each training pant 102 is transferred from the guide plate to the nip roll. The guide plate flanges 314 can be positioned closer to the main folding drum 212 than the guide plate central section 312, and the nip roll flanges 322 can be positioned closer to the main folding drum than the nip roll central section 320.

The contoured nip roll 222 can be rotatively mounted on a shaft 324 which, in turn, is operatively connected to a drive mechanism (not shown). The nip roll shaft 324 can be rotatively mounted to the support structure 240 with brackets 326 or other suitable devices. At one or more radial locations, the sidewalls 321 and flanges 322 can be cut out to form recesses 328. Rotation of the main folding drum 212 and the contoured nip roll 222 can be timed so that the retractable pins 282 are disposed in the recessed portions 328 as the pins pass through the tangent point between the main folding drum and the contoured nip roll.

The leading half 24 of the training pant 102 can be forced into contact with the contoured guide plate 220 and slid across the guide plate onto the contoured nip roll 222. The central portion or absorbent chassis 32 of the training pant 102 is desirably centrally positioned on the central section 312 of the guide plate 220. The side panels 134 can extend laterally outward from the absorbent chassis 32 and be disposed on the sidewalls 313 and flanges 314 of the guide plate 220. As the leading half 24 approaches the contoured nip roll 222, the elevation difference between the guide plate central section 312 and the flanges 314 cause the first fastening components 82 and 83 to move above the plane of the absorbent chassis 32 and move laterally inward toward the longitudinal center line 48 of the training pant. The leading half 24 of the training pant 102 can then be transferred to the contoured nip roll 222 having a similar configuration.

Entering the nip 224 between the main folding drum 212 and the contoured nip roll 222, the first fastening components 82 and 83 on the leading half 24 are directed inward toward the trailing half 22 of the training pant 102. Similarly the second fastening components 84 and 85 on the trailing half 22 are facing inward toward the leading half 24, as a result of having been previously folded 180 degrees by the side panel folding apparatus 210. The contour of the guide plate 220 and nip roll 222 can be established so that the elevation difference between the central sections 312 and 320 and the flanges 314 and 322 causes the first fastening components 82 and 83 to move laterally inward to the cross-machine direction location of the second fastening components 84 and 85. In the illustrated embodiment, the fastening components 82 and 83 on the leading half 24 are disposed on the inner surface 28 of the training pant 102 and are separated from one another by an initial transverse distance. The fastening components 84 and 85 on the trailing half 22 are disposed on the outer surface 30 of the training pant 102 and are separated from one another by substantially the same initial transverse distance. The fastening components 84 and 85 on the trailing half 22 can be inverted which causes the distance between the fastening components 84 and 85 to be reduced to a post inversion distance. The fastening components 82 and 83 on the leading half 24 are transversely displaced toward one another due to contact with the contoured guide plate 220 and/or contoured roll 222, resulting in a post displacement distance less than the initial distance. In particular embodiments, the post displacement distance can be equal to or substantially equal to the post inversion distance.

The nip 224 between the main folding drum 212 and the contoured nip roll can cause the fastening components 82–85 to engage one another. More specifically, the flanges 322 of the contoured nip roll 222 can be spaced sufficiently close to the main folding drum 212 to engage the fastening components 82–85.

Vacuum can be maintained on the trailing half 24 of the training pant 102 until the training pant is transferred to the exit conveyor 226 or other suitable handling means. The retractable pin mechanism 218 can be retracted prior to reaching the exit conveyor 226, and preferably between the tangent point between the main folding drum 212 and the contoured nip roll 222 and the location where the continuous vacuum belt 232 separates from the main folding drum.

FIG. 3 illustrates an alternative folding and seaming section that is similar in many respects to the folding and seaming section shown in FIG. 2. The embodiment shown in FIG. 3 includes an additional vacuum infeed conveyor 400 that can be used to provide a smooth transfer to the main folding drum 212. The trailing side panels or both the leading and trailing side panels can continue to be folded on the entry conveyor 208. The secondary folding drum 214 can be positioned to allow sufficient time for pin extension, for example, providing about 55 degrees of main folding drum rotation from the additional infeed conveyor 400 to the secondary folding drum.

FIG. 3 also illustrates that the contoured nip roll 222 can be sized to accommodate two products per revolution. In particular embodiments, the contoured nip roll 222 can comprise a vacuum roll that is adapted to provide vacuum just prior to the nip 224 with the main folding drum 212. Following the contoured nip roll 222, a series of rolls 402 can be disposed in close proximity to the main folding drum 212 to support the pants 20 as they rotate to the exit conveyors 226. The rolls 402, which may be driven rolls or free spinning idlers, can be employed to provide greater time for pin retraction. For example, there can be about 68 degrees of main folding drum rotation from the contoured nip roll 222 to the exit conveyors 226. The initial exit conveyor 226 can be provided with a vacuum nose roll 404 to pull the pants off the main folding drum 212.

A variant of the embodiment illustrated in FIG. 3 eliminates the contoured guide plate 220 and transfers the leading half 24 directly from the secondary folding drum 214 to the contoured nip roll 222. In this case, the secondary folding drum 214 and contoured nip roll 222 can be moved still closer together. The contoured nip roll 222 can comprise a vacuum roll, and the vacuum can be initiated as the leading half 24 begins to slip on or is released from the secondary folding drum 214.

Pants having a wide variety of configurations can be manufactured using the processes disclosed herein. Such configurations can include, among others, pants having the front and back waist regions of the same width, pants with one waist region wider than the other, pants with refastenable seams that are disposed at the sides of the wearer, pants with refastenable seams that are disposed forward or backward from the sides of the wearer, pants formed with fasteners initially on the same major surface, and pants formed with fasteners initially on opposite major surfaces. The processes disclosed herein can be adapted to accommodate any such pant configurations. Moreover, either waist region can be inverted and/or transversely displaced, and a waist region that is wider, narrower, or the same width as the other waist region can be inverted and/or transversely displaced. It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A process for making a prefastened and refastenable garment, comprising:
   transporting a discrete article in a primary direction of movement, the discrete article defining a leading half comprising first fastening components, a trailing half comprising second fastening components releasably engageable with the first fastening components, and an interconnecting region disposed between and interconnecting the leading and trailing halves;
   temporarily diverting the leading half from the primary direction of movement while continuing to transport the interconnecting region and the trailing half in the primary direction of movement;
   reestablishing movement of the leading half in the primary direction of movement;
   contacting the leading half with a contoured surface, wherein the first fastening components are transversely displaced toward one another; and
   moving the transversely displaced first fastening components into contact with the second fastening components.

2. The process of claim 1, wherein the leading half comprises a center panel and opposite side panels, and the contoured surface causes the side panels to become elevated relative to the center panel.

3. The process of claim 1, wherein contacting the leading half with the contoured surface causes the distance between the first fastening components to be reduced from an initial distance to a post displacement distance, the post displacement distance corresponding to the distance between the second fastening components.

4. The process of claim 1, further comprising folding side panels of the trailing half to invert the second fastening components.

5. The process of claim 4, wherein contacting the leading half with the contoured surface causes the distance between the first fastening components to be reduced from an initial distance to a post displacement distance, the post displacement distance being substantially equal to a post inversion distance between the inverted second fastening components.

6. The process of claim 4, wherein the discrete article has opposite first and second major surfaces, the first fastening components are disposed on the first surface and separated from one another by an initial distance, the second fastening components are disposed on the second surface and separated from one another by substantially the same initial distance, contacting the leading half with the contoured surface causes the distance between the first fastening components to be reduced from the initial distance to a post displacement distance, and folding the side panels in the trailing half causes the distance between the second fastening components to be reduced from the initial distance to a post inversion distance substantially equal to the post displacement distance.

7. The process of claim 1, wherein the first and second fastening components are disposed on opposite major surfaces of the discrete article.

8. The process of claim 1, wherein the second fastening components comprise hook material.

9. A process for making a prefastened and refastenable garment, comprising:
   transporting a discrete article on a primary transport surface in a primary direction of movement, the discrete article defining a leading half comprising first fastening components, a trailing half comprising second fastening components releasably engageable with the first fastening components, and an interconnecting region disposed between and interconnecting the leading and trailing halves;
   drawing the leading half onto a secondary transport surface traveling in a secondary direction of movement divergent from the primary direction of movement while continuing to transport the interconnecting region and the trailing half in the primary direction of movement;
   releasing the leading half from the secondary transport surface;
   contacting the leading half with a contoured surface, wherein the first fastening components are transversely displaced toward one another; and
   pressing the leading and trailing halves together with the transversely displaced first fastening components releasably engaging the second fastening components.

10. The process of claim 9, wherein contacting the leading half with the contoured surface causes the distance between the first fastening components to be reduced from an initial distance to a post displacement distance, the post displacement distance corresponding to the distance between the second fastening components.

11. The process of claim 9, further comprising folding side panels of the trailing half to invert the second fastening components.

12. The process of claim 11, wherein contacting the leading half with the contoured surface causes the distance between the first fastening components to be reduced from an initial distance to a post displacement distance, the post displacement distance being substantially equal to a post inversion distance between the inverted second fastening components.

13. The process of claim 11, wherein the discrete article has opposite first and second major surfaces, the first fastening components are disposed on the first surface and separated from one another by an initial distance, the second fastening components are disposed on the second surface and separated from one another by substantially the same initial distance, contacting the leading half with the contoured surface causes the distance between the first fastening components to be reduced from the initial distance to a post displacement distance, and folding the side panels in the trailing half causes the distance between the second fastening components to be reduced from the initial distance to a post inversion distance substantially equal to the post displacement distance.

14. The process of claim 9, wherein the leading half comprises opposite side panels and a center panel therebetween, the trailing half comprises opposite side panels and a center panel therebetween, and the first and second fastening components are disposed on the respective side panels.

15. The process of claim 9, wherein the first and second fastening components are disposed on opposite major surfaces of the discrete article.

16. A process for making prefastened and refastenable garments, comprising:
providing main and secondary folding drums in close proximity to one another and defining a tangent point therebetween;
rotating the main and secondary folding drums in opposite directions;
introducing a plurality of discrete articles onto the main folding drum, each discrete article defining a leading half comprising first fastening components, a trailing half comprising second fastening components releasably engageable with the first fastening components, and an interconnecting region disposed between and interconnecting the leading and trailing halves;
drawing the leading half of a discrete article onto the secondary folding drum as the leading half passes the tangent point, and continuing to transport the interconnecting region and the trailing half on the main folding drum;
releasing the leading half from the secondary folding drum such that the interconnecting region remains on the main folding drum;
contacting the leading half with a contoured surface, wherein the first fastening components are transversely displaced toward one another; and
pressing the leading and trailing halves together with the transversely displaced first fastening components releasably engaging the second fastening components.

17. The process of claim 16, wherein contacting the leading half with the contoured surface causes the distance between the first fastening components to be reduced from an initial distance to a post displacement distance, the post displacement distance corresponding to the distance between the second fastening components.

18. The process of claim 16, further comprising folding side panels of the trailing half to invert the second fastening components.

19. The process of claim 18, wherein contacting the leading half with the contoured surface causes the distance between the first fastening components to be reduced from an initial distance to a post displacement distance, the post displacement distance being substantially equal to a post inversion distance between the inverted second fastening components.

20. The process of claim 18, wherein the discrete articles have opposite first and second major surfaces, the first fastening components are disposed on the first surface and separated from one another by an initial distance, the second fastening components are disposed on the second surface and separated from one another by substantially the same initial distance, contacting the leading half with the contoured surface causes the distance between the first fastening components to be reduced from the initial distance to a post displacement distance, and folding the side panels in the trailing half causes the distance between the second fastening components to be reduced from the initial distance to a post inversion distance substantially equal to the post displacement distance.

21. The process of claim 16, wherein the leading half is forced into contact with a contoured guide plate.

22. The process of claim 21, wherein the leading half comprises a center panel and opposite side panels, the contoured guide plate comprises a central section and a pair of flanges outward of the central section, and contacting the leading half with the contoured guide plate causes the center panel to be positioned on the central section and the side panels to be positioned on the flanges.

23. The process of claim 16, wherein the leading half is forced into contact with a contoured roll.

24. The process of claim 23, wherein the fastening components are forced into engagement as they pass through a nip formed between the main folding drum and the contoured roll.

25. The process of claim 16, wherein the secondary folding drum is operatively connected to a source of vacuum to draw the leading half onto the secondary folding drum as the leading half passes the tangent point.

26. The process of claim 16, wherein the discrete articles are held on the main folding drum with vacuum, and the vacuum holding each leading half on the main folding drum is interrupted when the leading half reaches the tangent point.

27. The process of claim 16, further comprising mechanically holding the interconnecting region on the main folding drum.

28. The process of claim 27, wherein the discrete articles are sandwiched between retractable pins and the main folding drum when the retractable pins are extended.

29. The process of claim 16, wherein the first and second fastening components are disposed on opposite major surfaces of the discrete articles.

30. The process of claim 16, wherein the fastening components comprise separate elements bonded to side panels of the leading and trailing halves.

* * * * *